US007399625B2

(12) United States Patent
Kaku et al.

(10) Patent No.: US 7,399,625 B2
(45) Date of Patent: Jul. 15, 2008

(54) SCYTALONE DEHYDROGENASE GENE SHOWING TOLERANCE TO AGRICULTURAL PESTICIDE

(75) Inventors: Koichiro Kaku, Shizuoka (JP); Satoshi Watanabe, Shizuoka (JP); Kiyoshi Kawai, Shizuoka (JP); Tsutomu Shimizu, Shizuoka (JP); Kozo Nagayama, Shizuoka (JP)

(73) Assignee: Kumiai Chemical Industry Co., Ltd., Tokyo (JP)

(*) Notice: Subject to any disclaimer, the term of this patent is extended or adjusted under 35 U.S.C. 154(b) by 260 days.

(21) Appl. No.: 10/507,132

(22) PCT Filed: Feb. 24, 2003

(86) PCT No.: PCT/JP03/01980

§ 371 (c)(1),
(2), (4) Date: Sep. 10, 2004

(87) PCT Pub. No.: WO03/076628

PCT Pub. Date: Sep. 18, 2003

(65) Prior Publication Data

US 2006/0223136 A1 Oct. 5, 2006

(30) Foreign Application Priority Data

Mar. 12, 2002 (JP) ............................ 2002-066955

(51) Int. Cl.

| | |
|---|---|
| ***C07H 21/00*** | (2006.01) |
| ***C12N 15/00*** | (2006.01) |
| ***C12N 5/10*** | (2006.01) |
| ***C12N 5/04*** | (2006.01) |
| ***C12N 5/06*** | (2006.01) |
| ***C12N 1/21*** | (2006.01) |
| *C12N 9/88* | (2006.01) |
| *C12P 21/06* | (2006.01) |
| *C07K 14/00* | (2006.01) |

(52) U.S. Cl. ................. 435/232; 435/320.1; 435/252.3; 435/325; 435/69.1; 435/410; 530/350; 536/23.2; 536/23.1

(58) Field of Classification Search ................ 435/232, 435/320.1, 252.3, 325, 69.1, 410; 536/23.2, 536/23.1, 350
See application file for complete search history.

(56) References Cited

OTHER PUBLICATIONS

Branden et al., Introduction to Protein Structure, Garland Publishing Inc., New York, p. 247, 1991.*
Seffernick et al., J. Bacteriol. 183(8):2405-2410, 2001.*
Witkowski et al., Biochemistry 38:11643-11650, 1999.*
Wigley et al., Reprod. Fert. Dev. 6:585-588, 1994.*
Cameron, E., Molecular Biotechnology 7:253-265, 1997.*
Mullins et al., J. Clin. Invest. 97(7):1557-1560, 1996.*
Mullins et al., Hypertension 22(4):630-633, 1993.*
Meinkoth and Wahl, Current Protocols in Molecular Biology, Hybridization Analysis of DNA Blots, pp. 2.10.8-2.10.11, 1993.*
Motoyama, T., et al., cDNA cloning, expression, and mutagenesis of scytalone dehydratase needed for pathogenicity of the rice blast fungus, Pyricularia oryzae., Biosci. Biotechnol. Biochem. 1998, vol. 62, No. 3, pp. 564 to 566.
Nakasako, M., et al., Cryogenic X-ray crystal structure analysis for the complex of scytalone dehydratase of a rice blast fungus and its tight-binding inhibitor, carpropamid: the structural basis of tight-binding inhibition., Biochemistry 1998, vol. 37, pp. 9931 to 9939.

* cited by examiner

*Primary Examiner*—Delia M Ramirez
(74) *Attorney, Agent, or Firm*—Birch, Stewart, Kolasch & Birch, LLP

(57) ABSTRACT

The present invention provides a gene that can be used extensively in studies relating to resistant rice blast fungi. The gene codes for either one of the following proteins (a) or (b): (a) a protein consisting of the amino acid sequence shown in SEQ ID NO:2; or (b) a protein consisting of an amino acid sequence shown in SEQ ID NO:2 by deletion, substitution or addition of one or more amino acids, which exhibits scytalone dehydratase activity in the presence of a scytalone dehydratase inhibitor.

10 Claims, 10 Drawing Sheets
(1 of 10 Drawing Sheet(s) Filed in Color)

Fig.3

```
P. oryzae AB004741   -80 CTAGCAACCGCAGTGATACCCACACCAAAGAGCTTCCTTCAGTCTAGTATAGTTCACTTC   -21
Standard strain      -37 -------------------------------------------CTAGTATAGTTCACTTC   -21
Resistant strain     -30 --------------------------------------------------AGTTCACTTC   -21
                                                                  .......**********

                              ...
P. oryzae AB004741   -20 AACTTGTAAAAGCCGCCAACATGGGTTCGCAAGTTCAAAAGAGCGATGAGATAACCTTCT    40
Standard strain      -20 AACTTGTAAAAGCCGCCAACATGGGTTCGCAAGTTCAAAAGAGCGATGAGATAACCTTCT    40
Resistant strain     -20 AACTTGTAAAAGCCGCCAACATGGGTTCGCAAGTTCAAAAGAGCGATGAGATAACCTTCT    40
                         ************************************************************

P. oryzae AB004741    41 CAGACTACCTGGGCCTCATGACTTGCGTCTATGAGTGGGCAGACAGCTACGACTCCAAGG   100
Standard strain       41 CAGACTACCTGGGCCTCATGACTTGCGTCTATGAGTGGGCAGACAGCTACGACTCCAAGG   100
Resistant strain      41 CAGACTACCTGGGCCTCATGACTTGCGTCTATGAGTGGGCAGACAGCTACGACTCCAAGG   100
                         ************************************************************

P. oryzae AB004741   101 ACTGGGATAGGCTGCGAAAGGTCATTGCGCCTACTCTGCGCATTGACTACCGCTCCTTCC   160
Standard strain      101 ACTGGGATAGGCTGCGAAAGGTCATTGCGCCTACTCTGCGCATTGACTACCGCTCCTTCC   160
Resistant strain     101 ACTGGGATAGGCTGCGAAAGGTCATTGCGCCTACTCTGCGCATTGACTACCGCTCCTTCC   160
                         ************************************************************

P. oryzae AB004741   161 TCGACAAGCTCTGGGAGGCAATGCCGGCCGAGGAGTTCGTCGGCATGGTCTCGAGCAAGC   220
Standard strain      161 TCGACAAGCTCTGGGAGGCAATGCCGGCCGAGGAGTTCGTCGGCATGGTCTCGAGCAAGC   220
Resistant strain     161 TCGACAAGCTCTGGGAGGCAATGCCGGCCGAGGAGTTCGTCGGCATGGTCTCGAGCAAGC   220
                         ************************************************************

P. oryzae AB004741   221 AGGTGCTGGGCGACCCCACCCTCCGCACGCAGCACTTCATCGGCGGCACGCGCTGGGAGA   280
Standard strain      221 AGGTGCTGGGCGACCCCACCCTCCGCACGCAGCACTTCATCGGCGGCACGCGCTGGGAGA   280
Resistant strain     221 AGATGCTGGGCGACCCCACCCTCCGCACGCAGCACTTCATCGGCGGCACGCGCTGGGAGA   280
                         **.*********************************************************

P. oryzae AB004741   281 AGGTGTCCGAGGACGAGGTCATCGGCTACCACCAGCTGCGCGTCCCGCACCAGAGGTACA   340
Standard strain      281 AGGTGTCCGAGGACGAGGTCATCGGCTACCACCAGCTGCGCGTCCCGCACCAGAGGTACA   340
Resistant strain     281 AGGTGTCCGAGGACGAGGTCATCGGCTACCACCAGCTGCGCGTCCCGCACCAGAGGTACA   340
                         ************************************************************

P. oryzae AB004741   341 AGGACACCACCATGAAGGAGGTCACCATGAAGGGCCACGCCCACTCGGCAAACCTTCACT   400
Standard strain      341 AGGACACCACCATGAAGGAGGTCACCATGAAGGGCCACGCCCACTCGGCAAACCTTCACT   400
Resistant strain     341 AGGACACCACCATGAAGGAGGTCACCATGAAGGGCCACGCCCACTCGGCAAACCTTCACT   400
                         ************************************************************

P. oryzae AB004741   401 GGTACAAGAAGATCGACGGCGTCTGGAAGTTCGCCGGCCTCAAGCCCGATATCCGCTGGG   460
Standard strain      401 GGTACAAGAAGATCGACGGCGTCTGGAAGTTCGCCGGCCTCAAGCCCGACATCCGCTGGG   460
Resistant strain     401 GGTACAAGAAGATCGACGGCGTCTGGAAGTTCGCCGGCCTCAAGCCCGACATCCGCTGGG   460
                         *************************************************.**********

                                                                             ...
P. oryzae AB004741   461 GCGAGTTCGACTTTGACAGGATCTTTGAGGACGGACGGGAGACCTTTGGCGACAAATAAA   520
Standard strain      461 GCGAGTTCGACTTTGACAGGATCTTTGAGGACGGACGGGAGACCTTTG------------   508
Resistant strain     461 GCGAGTTCGACTTTGACAGGATCTTTGAGGACGGACGGGAGACCTTTG------------   508
                         ************************************************
```

Fig.4

```
P. oryzae AB004741 -80 CTAGCAACCGCAGTGATACCCACACCAAAGAGCTTCCTTCAGTCTAGTATAGTTCACTTC  -21
Standard strain    -46 ----------------------------------TCCTTCAGTCTAGTATAGTTCACTTC  -21
Resistant strain   -47 ---------------------------------TTCCTTCAGTCTAGTATAGTTCACTTC  -21
                                                       ........*****************

                                                             ...
P. oryzae AB004741 -20 AACTTGTAAAAGCCGCCAACATGGGTTCGCAAGTTCAAAAGAGCGATGAGATAACCTTCT   40
Standard strain    -20 AACTTGTAAAAGCCGCCAACATGGGTTCGCAAGTTCAAAAGAGCGATGAGATAACCTTCT   40
Resistant strain   -20 AACTTGTAAAAGCCGCCAACATGGGTTCGCAAGTTCAAAAGAGCGATGAGATAACCTTCT   40
                       ************************************************************

P. oryzae AB004741  41 CA----------------------------------------------------------   42
Standard strain     41 CAGGTGAGCATAATATCCCCCTCCAAAAAGAAAATAGCGGTGAAGCCACCAACGACAGTA  100
Resistant strain    41 CAGGTGAGCATAATATCCCCCTCCAAAAAGAAAATAGCGGTGAAGCCACCAACGACAGTA  100
                       **..........................................................

P. oryzae AB004741  43 -----------------------GACTACCTGGGCCTCATGACTTGCGTCTATGAGTGGG   79
Standard strain    101 CCGCTGACCCTAATTCCCCTCCAGACTACCTGGGCCTCATGACTTGCGTCTATGAGTGGG  160
Resistant strain   101 CCGCTGACCCTAATTCCCCTCCAGACTACCTGGGCCTCATGACTTGCGTCTATGAGTGGG  160
                       .......................*************************************

P. oryzae AB004741  80 CAGACAGCTACGACTCCAAGGACTGGGATAGGCTGCGAAAGGTCATTGCGCCTACTCTGC  139
Standard strain    161 CAGACAGCTACGACTCCAAGGACTGGGATAGGCTGCGAAAGGTCATTGCGCCTACTCTGC  220
Resistant strain   161 CAGACAGCTACGACTCCAAGGACTGGGATAGGCTGCGAAAGGTCATTGCGCCTACTCTGC  220
                       ************************************************************

P. oryzae AB004741 140 GC----------------------------------------------------------  141
Standard strain    221 GCGTATGTTCCGCCCTGCCATGTTTATTTTTACTTTCCCACACCAAATCCAGACTTTAAC  280
Resistant strain   221 GCGTATGTTCCGCCCTGCCATGTTTATTTTTACTTTCCCACACCAAATCCAGACTTTAAC  280
                       **..........................................................

P. oryzae AB004741 142 -------------------------------ATTGACTACCGCTCCTTCCTCGACAAGCT  170
Standard strain    281 AGCGACGACCAAAAAAAAAAAAAAAAAACAGATTGACTACCGCTCCTTCCTCGACAAGCT  340
Resistant strain   328 AGCGACGACCAAAAAAAAAAAAAA----CAGATTGACTACCGCTCCTTCCTCGACAAGCT  336
                       ........................    ...*****************************

P. oryzae AB004741 171 CTGGGAGGCAATGCCGGCCGAGGAGTTCGTCGGCATGGTCTCGAGCAAGCAGGTGCTGGG  230
Standard strain    341 CTGGGAGGCAATGCCGGCCGAGGAGTTCGTCGGCATGGTCTCGAGCAAGCAGGTGCTGGG  400
Resistant strain   337 CTGGGAGGCAATGCCGGCCGAGGAGTTCGTCGGCATGGTCTCGAGCAAGCAGATGCTGGG  396
                       ****************************************************.*******

P. oryzae AB004741 231 CGACCCCACCCTCCGCACGCAGCACTTCATCGGCGGCACGCGCTGGGAGAAGGTGTCCGA  290
Standard strain    401 CGACCCCACCCTCCGCACGCAGCACTTCATCGGCGGCACGCGCTGGGAGAAGGTGTCCGA  460
Resistant strain   397 CGACCCCACCCTCCGCACGCAGCACTTCATCGGCGGCACGCGCTGGGAGAAGGTGTCCGA  456
                       ************************************************************

P. oryzae AB004741 291 GGACGAGGTCATCGGCTACCACCAGCTGCGCGTCCCGCACCAGAGGTACAAGGACACCAC  350
Standard strain    461 GGACGAGGTCATCGGCTACCACCAGCTGCGCGTCCCGCACCAGAGGTACAAGGACACCAC  520
Resistant strain   457 GGACGAGGTCATCGGCTACCACCAGCTGCGCGTCCCGCACCAGAGGTACAAGGACACCAC  516
                       ************************************************************

P. oryzae AB004741 351 CATGAAGGAGGTCACCATGAAGGGCCACGCCCACTCGGCAAACCTTCACTGGTACAAGAA  410
Standard strain    521 CATGAAGGAGGTCACCATGAAGGGCCACGCCCACTCGGCAAACCTTCACTGGTACAAGAA  580
Resistant strain   517 CATGAAGGAGGTCACCATGAAGGGCCACGCCCACTCGGCAAACCTTCACTGGTACAAGAA  576
                       ************************************************************

P. oryzae AB004741 411 GATCGACGGCGTCTGGAAGTTCGCCGGCCTCAAGCCCGATATCCGCTGGGGCGAGTTCGA  470
Standard strain    581 GATCGACGGCGTCTGGAAGTTCGCCGGCCTCAAGCCCGACATCCGCTGGGGCGAGTTCGA  640
Resistant strain   577 GATCGACGGCGTCTGGAAGTTCGCCGGCCTCAAGCCCGACATCCGCTGGGGCGAGTTCGA  636
                       *************************************** ********************

                                                                  ...
P. oryzae AB004741 471 CTTTGACAGGATCTTTGAGGACGGACGGGAGACCTTTGGCGACAAATAAATGCATGCATC  530
Standard strain    641 CTTTGACAGGATCTTTGAGGACGGACGGGAGACCTTTGGCGACAAA                700
Resistant strain   637 CTTTGACAGGATCTTTGAGGACGGACGGGAGACCTTTGGCGACAAA                696
                       **********************************************
```

SCYTALONE DEHYDROGENASE GENE SHOWING TOLERANCE TO AGRICULTURAL PESTICIDE

FIELD OF THE INVENTION

The present invention relates to a gene coding for scytalone dehydratase from a rice blast fungus, which is known as a pathogenic fungus for rice blast.

BACKGROUND ART

Rice blast caused by rice blast fungi (*pyricularia oryzae, Magnaporthe grisea*) is recognized in most countries where rice is cultivated. In particular, in regions having climates of high temperature and high humidity (e.g., Japan), rice blast is one of the most serious diseases in agricultural industry. For high yield rice cultivation, prevention of and disinfestation for rice blast are essential. Recently, as an alternative to agents with treatment effects, box-treatment agents having preventive effects are used for reducing the labor of farmers in prevention and disinfestation regarding rice blast fungi. Examples of such agents include scytalone dehydratase (hereinafter, simply referred to as "SCDH") inhibitors as typified by carpropamid ((1RS,3SR)-2,2-dichloro-N-((R)-1-(4-chlorophenyl)ethyl)-1-ethyl-3-methylcyclopropanecarboxamide)) (Kurahashi et al., *J. Pestic. Sci,* 23, 22-28, 1998; Motoyama et al., *J. Pestic. Sci,* 23, 58-61, 1998). SCDH is an enzyme that catalyzes the dehydration reaction from scytalone to 1,3,8-trihydroxynaphtalene (hereinafter, simply referred to as "1,3,8-THN") in melanin biosynthesis pathways.

When a rice blast fungus ruptures and invades a cuticular membrane of a rice leaf surface, the concentration of glycerol in the appressorium, an infection-specific organ, increases up to 80 atm. In order to enclose the glycerol within the appressorium, the melanin layer of the cell wall is essential (Kamakura et al., *KASEAA,* 39, 340-347, 2001). Inhibition of melanin biosynthesis prevents formation of the appressorium. Thus, SCDH inhibitors do not have a direct fungicidal action, but rather are non-fungicidal agents that exhibit prevention and disinfestation activities by suppressing pathogenicity.

An SCDH gene from a filamentous fungus was first elucidated with *Pyricularia oryzae*. The nucleotide sequence of this gene was not available to the public and only the three-dimensional structure of the SCDH protein was reported (Landquist et al., Structure, 2, 937-944, 1994). Thereafter, an SCDH gene from *Colletorichum lagenarium* (Kubo et al., Appl. Environment. Microbiol, 62, 4340-4344, 1996; Accession no. D86079), followed by SCDH genes from *Aspergillus fumigatus* (Tsai et al., Mol. Microbiol, 26, 175-183, 1997; Accession no. U95042), *Pyricularia oryzae* (Motoyama et al., Biosci. Biotech. Biochem, 62, 564-566, 1998; Accession no. AB004741) and *Ophiostoma floccosum* (Wang et al., Accession no. AF316575) were reported. A three-dimensional structure of an SCDH protein bound to carpropamid has also been reported (Nakasako et al., Biochemistry, 37, 9931-9939, 1998; Wawrzak et al., Proteins: Struct. Func. Genet, 35, 425-439, 1999).

DISCLOSURE OF INVENTION

Recently, rice blast fungi with decreased sensitivity to SCDH inhibitors such as carpropamid (hereinafter, referred to as "resistant rice blast fungi") have been discovered. As described above, since the SCDH inhibitors such as carpropamid are very important agents in rice cultivation, it is of the utmost concern to investigate sensitivity determinant factors in resistant rice blast fungi and to discover effective methods of prevention and disinfestation for the resistant rice blast fungi in order to maintain stable rice cultivation.

However, studies concerning resistant rice blast fungi, such as elucidation of the sensitivity determinants in the resistant rice blast fungi or localization of habitats of the resistant rice blast fungi have hardly been made at present.

In order to achieve the above-described objective, the present inventor has undertaken intensive research and succeeded in clarifying the sensitivity determinants in the resistant rice blast fungi, thereby completing the present invention.

Thus, the present invention encompasses the following.

(1) A gene coding for either one of the following proteins (a) or (b):

(a) a protein consisting of the amino acid sequence shown in SEQ ID NO:2; or (b) a protein consisting of an amino acid sequence shown in SEQ ID NO:2 by deletion substitution or addition of one or more amino acids, which exhibits scytalone dehydratase activity in the presence of a scytalone dehydratase inhibitor.

(2) A gene according to (1), wherein the scytalone dehydratase inhibitor inhibits dehydration reaction from scytalone to 1,3,8-trihydroxynaphtalene in a melanin biosynthesis pathway.

(3) A gene according to (1), wherein the scytalone dehydratase inhibitor is carpropamid.

(4) A scytalone dehydratase encoded by the gene of (1).

(5) A recombinant vector comprising the gene of (1).

(6) A transformant obtained by transformation of the recombinant vector of (5).

(7) A method for assessing sensitivity of a rice blast fungus to a scytalone dehydratase inhibitor, comprising the steps of:

(a) identifying an amino acid in an amino acid sequence of scytalone dehydratase in a subject rice blast fungus, which corresponds to valine at position 75 in the amino acid sequence shown in SEQ ID NO: 4; and (b) assessing sensitivity of the subject rice blast fungus to the scytalone dehydratase inhibitor based on the results of step (a).

(8) A method for assessing sensitivity according to (7), wherein when the amino acid identified in step (a) is methionine, the sensitivity of the subject rice blast fungus to the scytalone dehydratase inhibitor is assessed to be lower than that of a wild-type rice blast fungus in step (b).

(9) A kit for screening an inhibitor, comprising the scytalone dehydratase of (4).

(10) A kit for assessing a rice blast fungus resistant to a scytalone dehydratase inhibitor, comprising a pair of primers designed to flank a nucleotide sequence coding for an amino acid corresponding to valine at position 75 in the amino acid sequence shown in SEQ ID NO: 4.

(11) A kit for assessing a rice blast fungus resistant to a scytalone dehydratase inhibitor, comprising an oligonucleotide including a nucleotide sequence coding for an amino acid corresponding to valine at position 75 in the amino acid sequence shown in SEQ ID NO: 4.

Hereinafter, the present invention will be described in detail.

The gene according to the present invention codes for scytalone dehydratase (hereinafter, referred to as a "mutant SCDH enzyme") that exhibits scytalone dehydratase activity in the presence of a scytalone dehydratase inhibitor (hereinafter, referred to as an "SCDH inhibitor"). In the following description, scytalone dehydratase with decreased scytalone dehydratase activity in the presence of an SCDH inhibitor is simply referred to as an "SCDH enzyme" or a "wild-type SCDH enzyme."

Examples of the SCDH inhibitor include carpropamid (2,2-dichloro-N-(1-(4-chlorophenyl)ethyl)-1-ethyl-3-methylcyclopropanecarboxamide), fenoxanil (1-(2,4-dichlorophenyl)oxy-N-(1-cyano-1,2-dimethyl)propylethanecarboxamide), diclocymet (N-[1-(2,4-dichlorophenyl)ethyl]-1-cyano-2,2-dimethylpropanecarboxamide) and the like. The SCDH inhibitors are usually used as infection inhibitors for rice with rice blast fungus to inhibit activity of the SCDH enzyme. Specifically, the SCDH enzyme catalyzes, in the melanin biosynthesis pathway shown in FIG. 1, a dehydration reaction from scytalone to 1,3,8-trihydroxynaphtalene (hereinafter, simply referred to as "1,3,8-THN") and a dehydration reaction from vermelone to 1,8-dihydroxynaphtalene.

The SCDH inhibitor inhibits the activity of this SCDH enzyme to prevent formation of an appressorium in a rice blast fungus, thereby suppressing pathogenicity to rice. In other words, the SCDH inhibitor decreases infectivity of the rice blast fungus, and thus prevents an outbreak of rice blast. A mutant SCDH enzyme, however, exhibits the above-described enzyme activity even in the presence of the SCDH inhibitor and thus confers resistance to the SCDH inhibitor upon rice blast fungi. Accordingly, a rice blast fungus that expresses a mutant SCDH enzyme (hereinafter, referred to as a "resistant rice blast fungus" or a "resistant strain") does not allow inhibition of the melanin biosynthesis even in the presence of an SCDH inhibitor, and an appressorium can be formed to rupture and invade a cuticular membrane of the a leaf surface. Thus, resistant rice blast fungi show high infectivity even in the presence of the SCDH inhibitors.

Examples of the mutant SCDH enzyme include an enzyme having the amino acid sequence shown in SEQ ID NO:2. The mutant SCDH enzyme may have an amino acid sequence similar to SEQ ID NO:2 with one or more amino acids being deleted, substituted or added, which exhibits scytalone dehydratase activity in the presence of a scytalone dehydratase inhibitor. As used herein, the expression "one or more" means, for example, 1-30, preferably 1-20, and more preferably 1-10.

The enzyme activity of a wild-type SCDH enzyme or a mutant SCDH enzyme can be assessed by determining the dehydration reaction from scytalone to 1,3,8-THN or the dehydration reaction from vermelone to 1,8-dihydroxynaphtalene. Specifically, a reaction solution containing the wild-type SCDH enzyme or the mutant SCDH enzyme and a substrate (scytalone or vermelone) is used to develop an enzyme reaction. Then, a decrease in the substrate and/or an increase in the reaction product (1,3,8-THN or 1,8-dihydroxynaphtalene) is determined, thereby assessing the enzyme activity of the wild-type SCDH enzyme or the mutant SCDH enzyme.

Specifically, the enzyme reaction from scytalone to 1,3,8-THN may be determined spectroscopically. For example, the decrease in scytalone may be determined according to Motoyama et al., *J. Pestic. Sci,* 23, 58-61, 1998.

On the other hand, the increase in 1,3,8-THN may be determined by UV absorption spectra of the scytalone substrate and the 1,3,8-THN product at 340-360 nm (as shown in FIG. 2). Although the absorption of scytalone overlaps with the absorption of 1,3,8-THN at 200-300 nm, the absorption of scytalone at 340-360 nm is negligible. In the determination method using UV absorption spectra at 340-360 nm, a rate assay where the enzyme reaction is determined for 100 seconds is employed to determine the sensitivity of the wild-type SCDH enzyme or the mutant SCDH enzyme to the SCDH inhibitor.

According to this method, the enzyme reaction is proceeded in a reaction solution, to which a predetermined concentration of an SCDH inhibitor (e.g., carpropamid) has been added, to determine UV absorption spectrum at 340-360 nm, thereby determining a synthesized amount of the reaction product, 1,3,8-THN. The determined synthesized amount of 1,3,8-THN is divided by the synthesized amount of 1,3,8-THN in the absence of the SCDH inhibitor to obtain an inhibition rate of the SCDH inhibitor at that concentration. The concentration of the SCDH inhibitor is varied to determine the inhibition rates of the wild-type and mutant SCDH enzymes and calculate the $I_{50}$ value for each enzyme. From the $I_{50}$ value for the wild-type SCDH enzyme and the $I_{50}$ value for the mutant SCDH enzyme, R/S ratio is calculated to assess the sensitivity of the mutant SCDH enzyme to the SCDH inhibitor. For example, when the calculated R/S ratio is 2 or higher, the mutant SCDH enzyme may be defined to have lower sensitivity to the SCDH inhibitor as compared to that of the wild-type SCDH enzyme.

Determination of the enzyme activity of the mutant SCDH enzyme is not limited to the above-described method, and any method may be applied. The method for determining enzyme activity of the mutant SCDH enzyme may use, for example, quantification of the enzyme reaction product, 1,3,8-trihydroxynaphtalene, through HPLC analysis.

A gene coding for the mutant SCDH enzyme (hereinafter, referred to as a "mutant SCDH gene") may be obtained from either genome DNA with introns or cDNA without introns as long as it contains the nucleotide sequence coding for the above-described mutant SCDH enzyme.

The mutant SCDH gene can be obtained by PCR using primers designed based on the cDNA sequence of the SCDH enzyme from rice blast fungus and genome DNA from a rice blast fungus resistant to the SCDH inhibitor (hereinafter, referred to as a "resistant rice blast fungus"). The mutant SCDH gene may also be obtained by RT-PCR using the above-mentioned primers and mRNA extracted from the resistant rice blast fungus. The cDNA sequence of the SCDH enzyme from the rice blast fungus is known and described in Motoyama et al., Biosci. Biotech. Biochem, 62, 564-566, 1988 (DNA databank, Accession no. AB004741).

Examples of the mutant SCDH gene obtained according to such methods include the nucleotide sequence shown in SEQ ID NO: 1. The results of comparison between the nucleotide sequence (cDNA) of the mutant SCDH gene and that of a gene coding for wild-type SCDH enzyme (hereinafter, referred to as an "SCDH gene") are shown in FIG. 3. The results of comparison between the nucleotide sequence of the mutant SCDH gene in genome DNA and that of the SCDH gene are shown in FIG. 4. As shown in FIGS. 3 and 4, in the mutant SCDH gene, G (guanosine) at position 223 in the SCDH gene is altered homozygously by A (adenosine). This alteration means that valine (Val) at position 75 in the wild-type SCDH enzyme is mutated into methionine (Met).

As a result of comparing the nucleotide sequence of the mutant SCDH gene with that of the SCDH gene, T (thymidine) at position 450 was found to be mutated by C (cytidine) in the mutant SCDH gene. However, this alteration does not result in amino acid mutation.

From comparisons in FIGS. 3 and 4, the mutant SCDH gene was found to have an intron of 81 bases and an intron of approximate 89 bases between positions 42 and 43 and positions 141 and 142 in the amino acid sequence of the mutant SCDH enzyme, respectively. Since the latter intron (located between positions 141 and 142 in the amino acid sequence of the mutant SCDH enzyme) was followed by poly(A) strand, and when PCR was carried out, the resultant product had various lengths, exact length thereof was unable to be determined. Therefore, it is expressed as "about 89 bases."

The mutant SCDH gene is not limited to the nucleotide sequence shown in SEQ ID NO: 1, and may be any nucleotide sequence coding for a protein consisting of the amino acid sequence shown in SEQ ID NO: 2, or an amino acid sequence shown in SEQ ID NO: 2 by deletion substitution or addition of one or more amino acids, which exhibits scytalone dehydratase activity in the presence of a scytalone dehydratase inhibitor. Examples of such nucleotide sequence include a nucleotide sequence shown in SEQ ID NO: 1, which includes a nucleotide substitution that does not result in amino acid mutation.

The mutant SCDH gene may be a nucleotide sequence coding for a protein that exhibits scytalone dehydratase activity in the presence of a scytalone dehydratase inhibitor, and capable of hybridizing to a nucleotide sequence complementary to the nucleotide sequence shown in SEQ ID NO: 1 under stringent conditions. Stringent conditions mean, for example, a sodium concentration of 10-300 mM, preferably 20-100 mM, and a temperature of 25-70° C., preferably 42-55° C.

The mutant SCDH gene may be obtained by PCR using, as a template, genome DNA from a rice blast fungus that infects rice even in the presence of the SCDH inhibitor and a pair of primers with predetermined sequences. The genome DNA is prepared according to a method using CTBA (cetyltrimethylammonium bromide) as an extract solution, a method via SDS/phenol or phenol/chloroform extraction, or with a commercially available kit (e.g., the DNeasy Plant System from Qiagen, the Nucleon PhytoPure kit from Amersham Biosciences, etc.), although its preparation is not limited to these methods.

Furthermore, the mutant SCDH gene can be obtained by extracting total mRNA from a rice blast fungus that infects rice even in the presence of the SCDH inhibitor and using the total mRNA and a pair of primers having predetermined sequences in RT-PCR. Total mRNA can be extracted from a rice blast fungus, for example, by a guanidium method, an SDS-phenol method, phenol/chloroform extraction with the RNAeasy Total RNA System from Qiagen, the Quick Prep Micro mRNA Purification Kit or the Quick Prep Total RNA Extraction Kit from Amersham Biosciences, although its preparation is not limited to these methods.

The pair of primers used in the above-described PCR and RT-PCR may be designed to flank the SCDH gene based on the nucleotide sequence of genome DNA from, for example, a rice blast fungus deposited with s gene bank. The pair of primers may also be designed by further adding a functional sequence based on a nucleotide sequence of genome DNA from a rice blast fungus. Examples of functional sequences include a sequence recognized by a restriction enzyme for linking to a vector, and an insertion sequence for reading frame adjustment.

Examples of the pair of primers include, but are not limited to, the following sequences:

```
Primer 1 (SEQ ID NO: 5):
5'-GCAGTGATACCCACACCAAAG-3'

Primer 2 (SEQ ID NO: 6):
5'-TTATTTGTCGGCAAAGGTCTCC-3'

Primer 3 (SEQ ID NO: 7):
5'-AGTTCGAACTGGAATTCAACCGGCACGCATGATGCATGCATTTA-3'

Primer 4 (SEQ ID NO: 8):
5'-ATGGGTTCGCAAGTTCAAAAG-3'
```

-continued

```
Primer 5 (SEQ ID NO: 9):
5'-GTGGCCCTTCATGGTGACCTCCT-3'

Primer 6 (SEQ ID NO: 10):
5'-ACAAGCTCTGGGAGGCAATG-3'

Primer 7 (SEQ ID NO: 11):
5'-ATCGTCGACGTGAATTCGTCTTGTAAAAGCCGCCAAC-3'
```

Primers 1, 4, 6 and 7 are sense primers while Primers 2, 3 and 5 are antisense primers. Therefore, one of the pair of primers is selected from the sense primers and the other is selected from the antisense primers.

Primer 2 is synthesized based on the nucleotide sequence disclosed in publication (Motoyama et al., Biosci. Biotech. Biochem, 62, 564-566, 1988), and the underlined base is "G." However, the corresponding base in Accession no. AB004741 from DNA data bank is "C." Although the correct base is "C," no effect is caused on the results from PCR and RT-PCR even when the base is "G." Underlined letters in Primers 3 and 7 indicate EcoRI recognized sequences. These EcoRI recognized sequences can be exploited upon incorporation into a protein expression vector or the like. Nucleotide sequences 5' to the EcoRI recognized sequences in Primers 3 and 7 are added to give enough margin for EcoRI to recognize the EcoRI recognized sequences. In Primer 7, two nucleotide sequences 3' to the EcoRI recognized sequences (i.e., "GT" at positions 18 and 19 in Primer 7) are nucleotides for allowing reading frame adjustment upon incorporation into a protein expression vector (pGEX-2T).

For example, RT-PCR is carried out using Primers 7 and 3 with total RNA as a template. The obtained PCR product is treated with EcoRI, and then incorporated into pGEX-2T (Amersham Biosciences) that has been subjected to EcoRI digestion and BAP treatment with alkaline phosphatase in advance, thereby preparing a plasmid. The plasmid was deposited with the International Patent Organism Depositary, National Institute of Advanced Industrial Science and Technology (Tsukuba Central 6, 1-1-1 Higashi, Tsukuba, Ibaraki, Japan) on Mar. 8, 2002 under the Budapest Treaty, as Rice Blast Mutant SCDH cDNA (FERM BP-7948).

This plasmid (Rice Blast Mutant SCDH cDNA) is capable of expressing an SCDH enzyme as a fusion protein with glutathione-S-transferase (hereinafter, referred to as "GST") in a host such as *E.coli*. A plasmid with a mutant SCDH gene may be constructed to be applicable to a cell-free protein expressing system.

Furthermore, the mutant SCDH gene may be obtained using a predetermined probe and a cDNA library from rice blast fungi that infect rice even in the presence of an SCDH inhibitor.

The mutant SCDH gene may also be obtained by mutagenesis of a wild-type SCDH gene. For example, a mutant SCDH gene may be obtained through the so-called site-directed mutagenesis using primers designed to alter a codon in a wild-type SCDH gene coding for valine (Val) at position 75 by a codon coding for methionine (Met). A commercially available kit may be used to obtain a mutant SCDH gene using the site-directed mutagenesis. Examples of commercially available kits include the TaKaRa LA PCR in vitro Mutagenesis kit (Takara).

The above-described mutant SCDH gene is useful for screening a novel SCDH inhibitor which decreases the infectivity of a resistant rice blast fungus, as illustrated in the Examples below. Specifically, an expression vector operatively incorporating the above-described mutant SCDH gene is used to express the mutant SCDH enzyme, the enzyme activity of which is in turn determined in the presence of a candidate agent for a novel SCDH inhibitor. By determining whether or not the enzyme activity of the mutant SCDH enzyme is decreased in the presence of the candidate agent, a novel SCDH inhibitor can be screened.

Specifically, according to conventional determination methods, inhibition of appressorium formation by a rice blast fungus in the presence of a candidate agent is assessed by a so-called pot test or a test based on observation of an appressorium involving the rupture of cellophane affixed on an agar petri dish, and thus these methods are hardly capable of rapid screening for an SCDH inhibitor. On the other hand, according to the above-described method, enzyme activity of an SCDH enzyme can be measured by a simple procedure, allowing rapid screening for a novel SCDH inhibitor.

From the nucleotide sequence analysis of the above-described mutant SCDH gene, it was found that the mutant SCDH enzyme in which valine (Val) at position 75 in the SCDH enzyme had been altered by methionine (Met) exhibited enzyme activity in the presence of the SCDH inhibitor. Therefore a nucleotide sequence coding for the amino acid at position 75 in the SCDH enzyme may be analyzed to determine whether the subject SCDH gene has conferred resistance to an SCDH inhibitor.

Specifically, when investigating whether or not a rice blast fungus, for example, from a predetermined region (a subject rice blast fungus) has sensitivity to an SCDH inhibitor, the amino acid at position 75 in the SCDH enzyme coded by the SCDH gene (the subject SCDH gene) from the subject rice blast fungus may be identified to assess the sensitivity of the subject rice blast fungus to the SCDH inhibitor.

The nucleotide sequence coding for the amino acid at position 75 in the subject SCDH enzyme may be identified according to any method and is not limited to a particular method. In order to sequence the nucleotide sequence coding for the amino acid at position 75 in the SCDH enzyme, for example, at least a pair of primers designed to flank the nucleotide sequence comprising the nucleotide sequence coding for the amino acid at position 75 in the SCDH enzyme and template DNA (cDNA or genome DNA) are used to sequence a predetermined region of the template DNA. Based on the sequenced nucleotide sequence, the amino acid at position 75 in the subject SCDH enzyme can be identified.

For sequencing the nucleotide sequence coding for the amino acid at position 75 in the subject SCDH enzyme, the genome DNA as the template is preferably obtained through solid cultivation of the subject rice blast fungus, followed by collection of filamentous mycelia and microwave irradiation of the mycelia. Irradiation with microwaves may be carried out, for example, using a microwave oven or the like. The genome DNA as the template can be obtained in a short time by this method, as compared to the standard method of harvesting the subject rice blast fungus after liquid culture and extracting genome DNA therefrom.

For determining the nucleotide sequence coding for the amino acid at position 75 in the subject SCDH enzyme, one of the primers is preferably designed to hybridize near, for example, a location 40 bases upstream from the nucleotide sequence coding for the amino acid at position 75. Consequently, the nucleotide sequence coding for the amino acid at position 75 in the subject SCDH enzyme can be determined in a short time.

Furthermore, for determining the nucleotide sequence coding for the amino acid at position 75 in the subject SCDH enzyme, an oligonucleotide comprising a nucleotide sequence coding for an amino acid corresponding to valine at position 75 in the amino acid sequence shown in SEQ ID NO: 4 may be used. For example, the oligonucleotide is designed to hybridize to the gene coding for the subject SCDH enzyme when the amino acid at position 75 in the subject SCDH enzyme is methionine. Then, via colony hybridization or Southern hybridization using this oligonucleotide as a probe, the amino acid at position 75 in the subject rice blast fungus may be identified. The sensitivity of the subject rice blast fungus to an SCDH inhibitor may also be assessed through this method.

Moreover, for analyzing the amino acid at position 75 in the subject SCDH enzyme, single-stranded DNA conformation polymorphism (hereinafter, referred to as "SSCP") may be exploited. Specifically, difference in mobility patterns between a wild-type SCDH gene and a resistance SCDH gene due to difference in single-stranded conformation is detected in advance, and compared to a mobility pattern based on the single-stranded conformation of the subject SCDH gene. Accordingly, the nucleotide sequence of the subject SCDH gene coding for the amino acid at position 75 in the SCDH enzyme can be identified. By exploiting SSCP for analyzing the amino acid at position 75 in the subject SCDH enzyme, sensitivity of the subject rice blast fungus to the SCDH inhibitor can be determined very quickly.

For analyzing the amino acid at position 75 in the subject SCDH enzyme, modified PCR-restriction fragment length polymorphism (RFLP) analysis (hereinafter, referred to as "modified PCR-RFLP method") may also be applied. Specifically, by modified PCR-RFLP analysis, mutation of valine (Val) at position 75 into methionine (Met) (hereinafter, referred to as "Val75Met mutation") in the SCDH enzyme from the subject rice blast fungus can be tested in a simple manner.

In the modified PCR-RFLP analysis, one of the primers used for PCR does not comprise the base at position 223 (the base contained in the codon coding for the amino acid at position 75 in the SCDH enzyme) and is designed to have a restriction-enzyme-recognized sequence at the 3'-end depending upon the type of the base at position 223. This primer may contain one or more bases partially mismatching the nucleotide sequence of the genome DNA or cDNA as the template, while containing the above restriction-enzyme-recognized sequence. The restriction-enzyme-recognized sequence is not particularly limited and may be a sequence recognized by XbaI.

According to the modified PCR-RFLP analysis, first, PCR is performed using a pair of primers designed as described above and genome DNA or cDNA as a template. Upon PCR, various conditions such as temperature or time may appropriately be determined so that the desired region of the template can be amplified even if a primer including one or more bases mismatching the template is used. The product resulting from PCR contains a restriction-enzyme-recognized sequence as well as the above-described primer depending on the base at position 223. The restriction-enzyme-recognized sequence may not be contained depending on the base at position 223.

Next, the product resulting from PCR is treated with a restriction enzyme that recognizes the restriction-enzyme-recognized sequence contained in the above-described primer The fragments obtained through this restriction enzyme treatment have different lengths due to the difference of the base at position 223. Then, the lengths of the fragments obtained by the restriction enzyme treatment may be detected, for example, by a method such as electrophoresis to identify the base at position 223 to analyze the amino acid at position 75 in the subject SCDH enzyme.

Furthermore, for analyzing the amino acid at position 75 in the subject SCDH enzyme, a generally known single nucleotide polymorphism typing method may be employed. Examples of the single nucleotide polymorphism typing method include the SNaPshot Multiplex Kit from Applied Biosystems (single primer extension reaction), the Masscode system from Qiagen (mass spectrometry), the MassARRAY system from Sequenom, the UCAN method from Takara, the Invader assay using Cleavase and a method using a microarray.

BRIEF DESCRIPTION OF THE DRAWINGS

The patent or application file contains at least one drawing executed in color. Copies of this patent or patent application publication with color drawing(s) will be provided by the office upon request and payment of the necessary fee.

FIG. 3 shows comparison between the nucleotide sequence of the SCDH gene from the rice blast fungus registered with the gene bank (SEQ ID NO: 13), a nucleotide sequence (cDNA) of an SCDH gene from a standard strain (SEQ ID NO: 14) and a nucleotide sequence (cDNA) of an SCDH gene from a resistant strain (SEQ ID NO: 15).

FIG. 4 shows comparison between the nucleotide sequence of the SCDH gene from the rice blast fungus registered with the gene bank (SEQ ID NO: 16), a nucleotide sequence (genome DNA) of an SCDH gene from a standard strain (SEQ ID NO: 17) and a nucleotide sequence (genome DNA) of an SCDH gene from a resistant strain (SEQ ID NO: 18).

BEST MODE FOR CARRYING OUT THE INVENTION

EXAMPLES

Hereinafter, the present invention will be described in more detail by means of examples. The technical scope of the present invention, however, is not limited by these examples.

Example 1

According to this example, first, filamentous mycelia used for extracting SCDH enzymes were prepared. Spore solutions ($10^5$/ml) containing a rice blast fungus (*Pyricularia oryzae*) as a standard (wild-type) strain and carpropamid-resistant rice blast fungi (resistant strains A and B) were individually added to 200 ml YGPCa liquid culture solutions (pH 6.5) each containing yeast extract (5 g), glucose (20 g), $KH_2PO_4$ (0.5 g), $Na_2HPO_4$ (0.5 g) and $CaCl_2$ (0.5 mg), and were grown at 27° C. for 4 to 5 days.

After the cultivation, the filamentous mycelia were collected through centrifugation of the culture solutions and washed with distilled water. Cold acetone, which has five times the weight of the mycelia, was added, and the results were homogenized with a Waring blender. The homogenates were centrifuged (15,000×g, 20 min.). The precipitates were dried at 4° C. to obtain acetone powders, which were stored at −85° C.

The obtained acetone powders were used to prepare crude enzyme solutions containing the SCDH enzymes in order to determine their enzyme activities. In order to prepare these crude enzyme solutions, each the acetone powder was suspended in 20 ml of 1⁄15 M potassium phosphate buffer (pH 6.8) agitated for 30 minutes while being iced and then centrifuged at 15,000×g for 15 minutes. Supernatants obtained by centrifugation were used as the crude enzyme solutions.

Next, to determine the enzyme activities of the SCDH enzymes using the crude enzyme solutions, first, 1,300 μl of 100 mM phosphate buffer (pH 6.8) containing 1 mM EDTA, 30 μl of 20 mM scytalone (ethanol solution), 30 μl ethanol solution of carpropamid at an appropriate concentration and 1,440 μl ultrapure water were mixed and pre-incubated at 27° C. for 2 minutes. Then, 200 μl of the crude enzyme solution was added to initiate enzyme reaction. The amount of 1,3,8-THN produced from scytalone through enzyme reaction was monitored for 100 seconds as an increase in the absorbance at UV 350 nm, thereby determining enzyme activity caused by the SCDH enzyme contained in the crude enzyme solution. The scytalone substrate was prepared from mycelium obtained through liquid cultivation of the standard (wild-type) strain in the presence of carpropamid, according to a routine technique (Kurahashi et al., J. Pestic. Sci, 23, 22-28, 1998).

Figure 1:
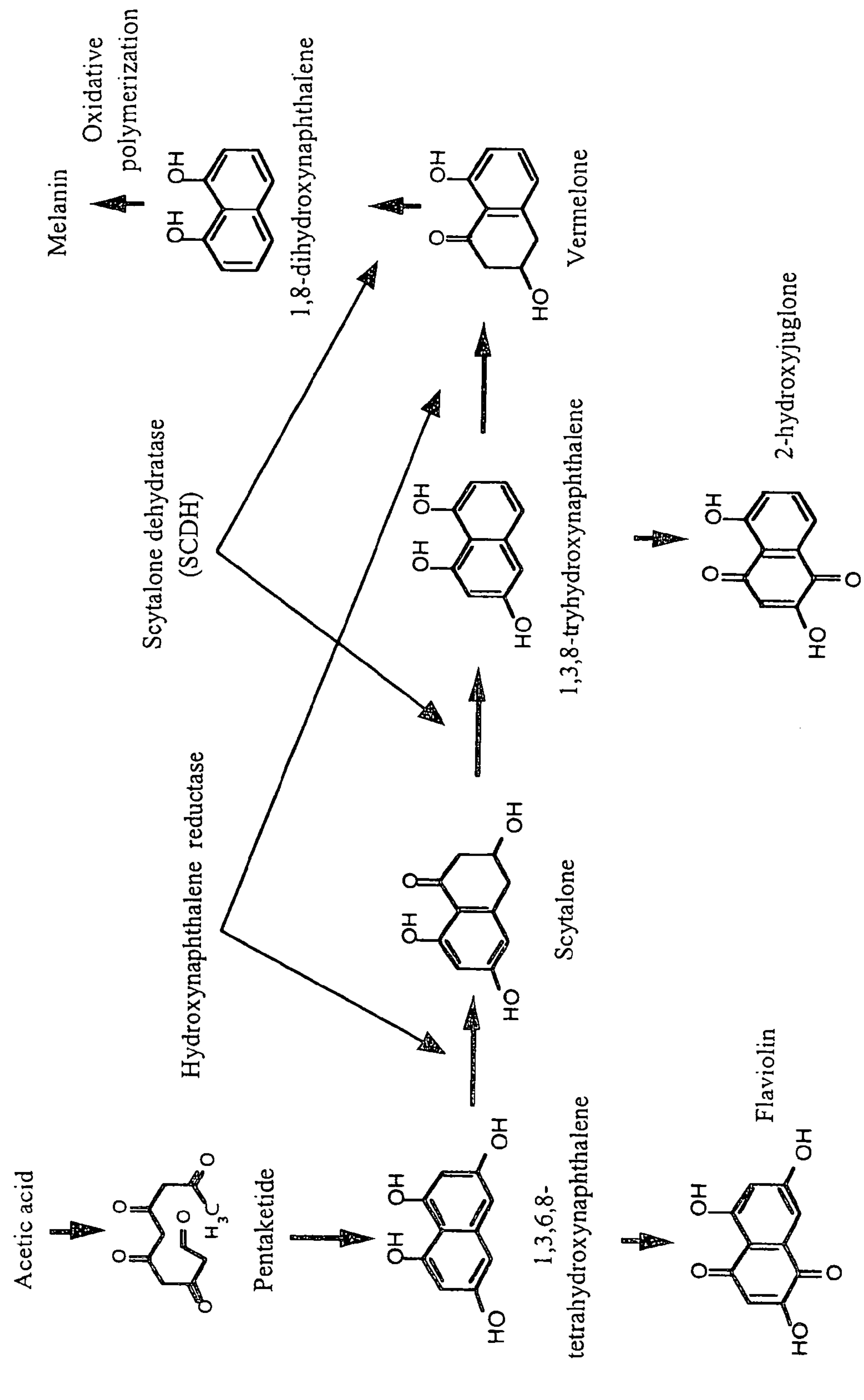
FIG. 1 is a diagram illustrating a melanin biosynthesis pathway in a rice blast fungus.
Figure 2:
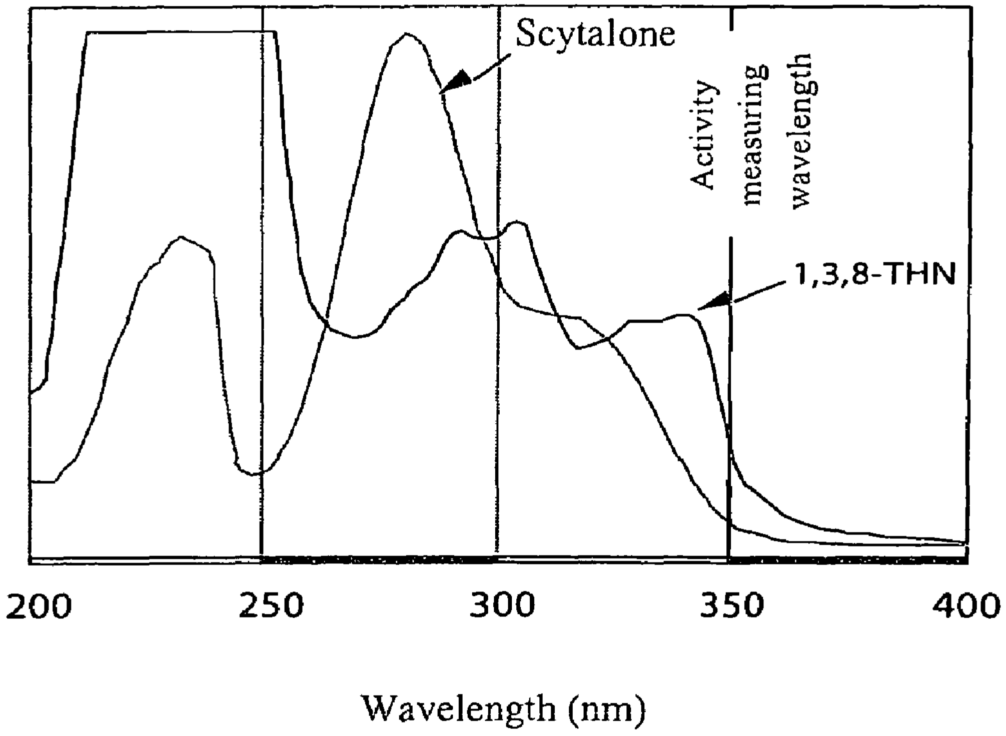
FIG. 2 is a characteristic diagram showing UV absorption spectra of scytalone and 1,3,8-THN.
Figure 5:
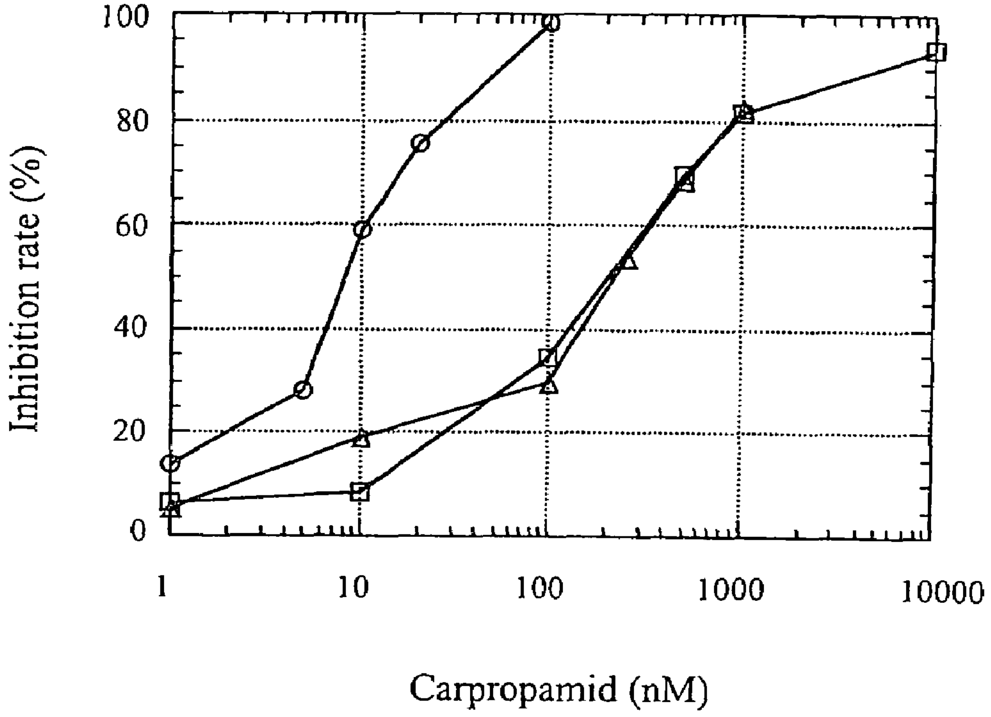
FIG. 5 is a characteristic diagram showing the relationship between the carpropamid concentrations and the inhibition rates for SCDH enzyme activity in crude enzyme solutions extracted from the standard strain and the resistant strains (A and B). In this diagram, the open circles represent the results for the crude enzyme solution from the standard strain, the open triangles represent the results for the crude enzyme solution from the resistant strain A and the open squares represent the results for the crude enzyme solution from the resistant strain B.

The results are shown in FIG. 5. These results were used to calculate 50% inhibition concentrations ($I_{50}$ values) by probit analysis. As a result, the $I_{50}$ value of the crude enzyme solution extracted from the standard (wild-type) strain with respect to carpropamid was 7.45 nM while those of the resistant strains A and B were 163 nM and 157 nM, respectively. From these values, the R/S ratio was about 21.5. This suggested that a factor for carpropamid resistance in the resistant strains A and B was the decrease in the sensitivity of scytalone dehydratase, which is the target of the carpropamid.

Example 2

In this example, first, filamentous mycelia were prepared as described below for extracting genome DNA and mRNA from rice blast fungi. First, a standard (wild-type) strain and carpropamid-resistant rice blast fungi (resistant strains A and B) were individually cultured on oatmeal media. After the cultivation, the mycelium parts were each added to 20 ml potato-dextrose (PD) liquid media and pre-cultured at 28° C. for 3 days. Since the pre-cultured filamentous mycelia form themselves into lumps, they were homogenized with a sterilized Waring blender and 1 ml of each sample was cultured in a 20 ml PD liquid medium for another 3-5 days. The mycelia were separated by filtration under reduced pressure and washed with distilled water. These mycelia were ground in liquid nitrogen using a mortar. The ground powders were stored at −85° C. Thus, powders from the standard (wild-type) strain, the resistant strain A and the resistant strain B were obtained.

For extracting total RNA using the powder from the resistant strain A, the Rneasy Plant Mini Kit (Qiagen) was used according to the attached protocol. For extracting genome DNA using the obtained powder, the Dneasy Plant Mini Kit (Qiagen) was used according to the attached protocol. The RNA concentration was quantified by determining the absorption at $OD_{260}$ with a spectrophotometer. DNA concentration was determined by observation of the brightness on 1% agarose gel or by measurements of the fluorescence spectrum using Hoe 33258 (Hoechst).

Next, the obtained total RNA was used to prepare cDNA containing a mutant SCDH gene from the resistant strain. In order to prepare cDNA containing the mutant SCDH gene, first, the obtained RNA (2 μg) was mixed with 2 μl oligo$(dT)_{20}$ (10 pmol/μl), 2 μl each of Primer 1 (5'-GCAGTGATACCCACACCAAAG-3', 25 pmol/μl) (SEQ ID NO: 5) and Primer 2 (5'-TTATTTGTCGGCAAAGGTCTCC-3', 25 pmol/μl) (SEQ ID NO: 6) and RT-PCR beads (Amersham Biosciences) to a final volume of 50 μl to prepare a reaction solution. The reaction took place under the following conditions. For cDNA synthesis, reaction was performed at 42° C. for 30 minutes, followed by reaction at 95° C. for 30 minutes. Subsequently, for PCR reaction using the synthesized cDNA as a template, 35 cycles of 95° C. for 30 seconds, 55° C. for 1 minute and 72° C. for 1 minute were repeated. After the final cycle at 72° C. for 7 minutes, the reaction was carried out and terminated. The reaction solution obtained was purified after the reaction using the GFX PCR DNA and the Gel Band Purification Kit (Amersham Biosciences) to obtain the RT-PCR product. cDNA containing the SCDH gene from the standard strain and cDNA containing the mutant SCDH gene from the resistant strain B were also obtained in manners similar to the above-described method.

In addition, DNA containing the mutant SCDH gene from the resistant strain A was prepared using the obtained genome DNA. For preparing this DNA, first, 4 μl of the obtained genome DNA was mixed with 1 μl each of Primer 1 (5'-GCAGTGATACCCACACCAAAG-3', 25 pmol/μl) (SEQ ID NO: 5) and Primer 3 (5'-AGTTCGAACTGGAATTCAACCGGCACGCATGATGCATGCATTTA-3', 25 pmol/μl) (SEQ ID NO: 7) and PCR beads (Amersham Biosciences) to a final volume of 25 μl to prepare a reaction solution. The reaction took place under the following conditions. For PCR reaction using the genome DNA as a template, 40 cycles of 95° C. for 30 seconds, 55° C. for 1 minute and 72° C. for 2 minutes were repeated. After the final cycle at 72° C. for 7 minutes, the reaction was carried out and terminated. The reaction solution obtained was purified after the reaction using the GFX PCR DNA and the Gel Band Purification Kit (Amersham Biosciences) to obtain the PCR product. DNA containing the SCDH gene from the standard strain and DNA containing the mutant SCDH gene from the resistant strain B were also obtained in manners similar to the above-described method.

Then, the obtained RT-PCR product and the PCR product were used to sequence the nucleotide sequence of cDNA containing the mutant SCDH gene and the nucleotide sequence of DNA containing the mutant SCDH gene. Sequencing was performed using the BigDye Terminator Cycle Sequencing FS Ready Reaction Kit from Applied Biosystems.

The sequencing reaction using this kit was performed in a reaction solution (total amount: 20 μl) of a mixture of the RT-PCR or the PCR product as a template, 3.2 pmol primers (Primers 1, 3, 5 and 6) and 8 μl of terminator pre-mix. As the reaction conditions, 40 cycles of 96° C. for 10 seconds, 50° C. for 5 seconds and 60° C. for 4 minutes were repeated. After the final cycle, the reaction was terminated at 60° C. for 7 minutes. After the reaction, the components such as the die terminator remaining in the reaction solution were removed by gel filtration using Auto Seq G-50 (Amersham Bioscience). Then, the reaction product was analyzed using ABI 310 Genetic Analyzer from Applied Biosystems for nucleotide sequencing. The nucleotide sequence of the mutant SCDH gene sequenced using the RT-PCR product as the template is shown in SEQ ID NO: 1 and the amino acid sequence of the mutant SCDH enzyme encoded by the mutant SCDH gene is shown in SEQ ID NO: 2.

The results from the analysis of cDNA of the mutant SCDH gene using the RT-PCR product as the template are shown in FIG. 3. FIG. 3 shows comparison between the nucleotide sequence of the SCDH gene from the rice blast fungus registered with the gene bank (Accession no. AB004741, upper row), the nucleotide sequence of the SCDH gene analyzed using the RT-PCR product obtained from the standard strain (middle row) and the nucleotide sequence of the mutant SCDH gene analyzed using the RT-PCR product obtained from the resistant strain A (bottom row).

The results from analysis of the mutant SCDH gene present in the genome DNA using the PCR product as the template are shown in FIG. 4. FIG. 4 shows comparison between the nucleotide sequence of the SCDH gene from the rice blast fungus registered with the gene bank (Accession no. AB004741, upper row), the nucleotide sequence of the SCDH gene analyzed using the PCR product obtained from the standard strain (middle row) and the nucleotide sequence of the mutant SCDH gene analyzed using the PCR product obtained from the resistant strain A (bottom row).

Referring to FIGS. 3 and 4, G (guanosine) at position 223 in the cDNA nucleotide sequence of the SCDH gene was found to have altered homozygously by A (adenosine) in the resistant strain A. This means that valine (Val) at position 75 in the amino acid sequence of the SCDH enzyme from the standard strain will be mutated into methionine (Met). The base at position 450 in the cDNA nucleotide sequence was T (thymidine) in the registered nucleotide sequence (Accession no. AB004741, upper row in FIG. 3) while it was C (cytidine) in the standard strain and the resistant strain. However, since the alteration of the base at position 450 in these cDNA nucleotide sequences is not associated with amino acid mutation, it presumably has nothing to do with sensitivity to SCDH inhibitors.

From FIG. 4, introns with lengths of 81 bases and about 89 bases were confirmed between positions 42 and 43 and positions 141 and 142, respectively, in the nucleotide sequence shown in SEQ ID NO: 3. Since the latter intron was followed by poly(A) strand and the products resulting from PCR had various lengths, the exact length thereof was unable to be determined. Accordingly, it is expressed as "about 89 bases."

Example 3

A simple assay of mutation of valine (Val) into methionine (Met) at position 75 (hereinafter, referred to as "Val75Met mutation") in the SCDH enzymes from rice blast fungi was considered.

A rice blast fungus grown on an oatmeal medium (5% oatmeal 2% sucrose and 1.5% agar) at 28° C. was pricked with a toothpick and transferred into a 1.5 μl microtube. The microtube was covered with a lid and irradiated with microwave in a microwave oven (600 W) for 5-7 minutes. Due to this treatment, the cell wall of the fungus was ruptured.

Next, 50 μl TE buffer (pH 8.0) was added to the microtube, and the resultant was thoroughly agitated and centrifuged at 14,000 rpm for 10 minutes. The supernatant containing free genome DNA was transferred to another microtube and stored at −20° C. One to five μl of the supernatant was mixed with 1 μl each of Primer 4 (5'-ATGGGTTCGCAAGTTCAAAAG-3', 25 pmol/μl) (SEQ ID NO: 8), Primer 5 (5'-GTGGCCCTTCATGGTGACCTCCT-3', 25 pmol/μl) (SEQ ID NO: 9) and PCR beads (Amersham Biosciences) for a final volume of 25 μl to prepare a reaction solution. For PCR reaction, 40 cycles of 95° C. for 30 seconds, 55° C. for 1 minute and 72° C. for 2 minutes were repeated. After the final cycle at 72° C. for 7 minutes, the reaction was carried out and terminated. The reaction solution was purified using the Invisorb Spin PCRapid Kit (Invitek) to obtain a PCR product. The PCR product contained in the reaction solution was subjected to sequencing reaction using the BigDye Terminator Cycle Sequencing FS Ready Reaction Kit from Applied Biosystems.

For the sequencing reaction, the PCR product as a template, 3.2 pmol of Primer 6 (5'-ACAAGCTCTGGGAGGCAATG-3') (SEQ ID NO: 10) and 8μl of terminator pre-mix were mixed to prepare a reaction solution for a total amount of 20 μl. For the sequencing reaction, 40 cycles of 96° C. for 10 seconds, 50° C. for 5 seconds and 60° C. for 4 minutes were repeated. After the final cycle at 60° C. for 7 minutes, the reaction was carried out and terminated. After the reaction, components such as the die terminator remaining in the reaction solution were removed by gel filtration using the Auto Seq G-50 (Amersham Bioscience). Then, the reaction product was subjected to sequence analysis using the ABI 310 Genetic Analyzer from Amersham Biosciences. By using a 47 cm×50 μm short capillary column from Amersham Biosciences, mutation of the amino acid valine at position 75 into methionine was confirmed in a short time of about 35 minutes per sample.

Example 4

A simple assay of mutation of valine (Val) into methionine (Met) at position 75 (hereinafter, referred to as Val75Met mutation) in an SCDH enzyme from a rice blast fungus was considered by applying a single-stranded DNA conformation polymorphism (SSCP) analysis.

As in Example 3, a genome DNA solution was simply prepared by irradiating rice blast fungus filamentous mycelium with microwaves. Five μl of this genome DNA solution were mixed with 1 μl each of Primer 6 (5'-ACAAGCTCTGGGAGGCAATG-3', 25 pmol/μl) (SEQ ID NO: 10), Primer 5 (5'-GTGGCCCTTCATGGTGACCTCCT-3', 25 pmol/μl) (SEQ ID NO: 9) and PCR bead (Amersham Biosciences) for a final volume of 25 μl to prepare a reaction solution. For PCR reaction, 40 cycles of 95° C. for 30 seconds, 55° C. for 1 minute and 72° C. for 2 minutes were repeated. After the final cycle, the reaction was terminated at 72° C. for 7 minutes. As a result of this reaction, 215 bp PCR product was obtained. The components such as taq DNA polymerase and primers remaining in the reaction solution were removed using GFX PCR DNA and the Gel Band Purification Kit (Amersham Biosciences).

Thereafter, a mixture of 0.4 ml of 0.5 M EDTA (pH 8.0), 10 mg of bromophenol blue and 10 ml of formamide was prepared as a loading buffer for SSCP. The reaction solution and the loading buffer were mixed at a ratio of 1:1, heated at 85° C. for 15 minutes and cooled at once. As a result, the PCR product contained in the reaction solution became single-stranded DNA.

Figure 6A:
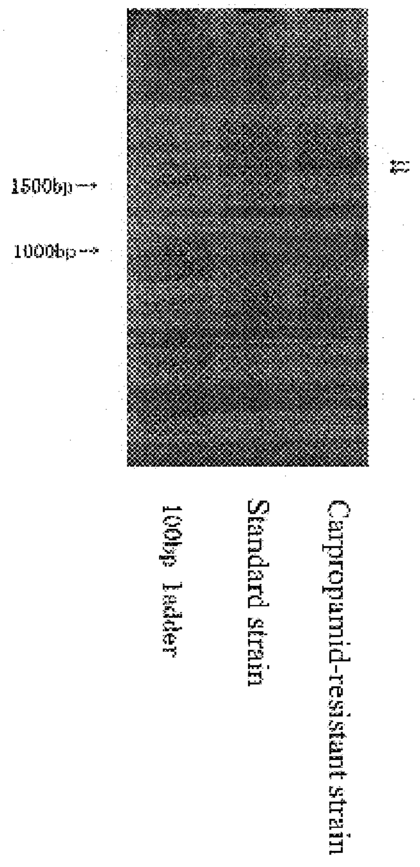
FIG. 6 are electrophoresis pictures showing the results from the single-stranded DNA conformation polymorphism (SSCP) analysis conducted in Example 4, where A (left) shows the results from electrophoresis without purification using GFX PCR DNA and Gel Band Purification Kit while B (right) shows the results from electrophoresis following purification using GFX PCR DNA and Gel Band Purification Kit.
Figure 6B:
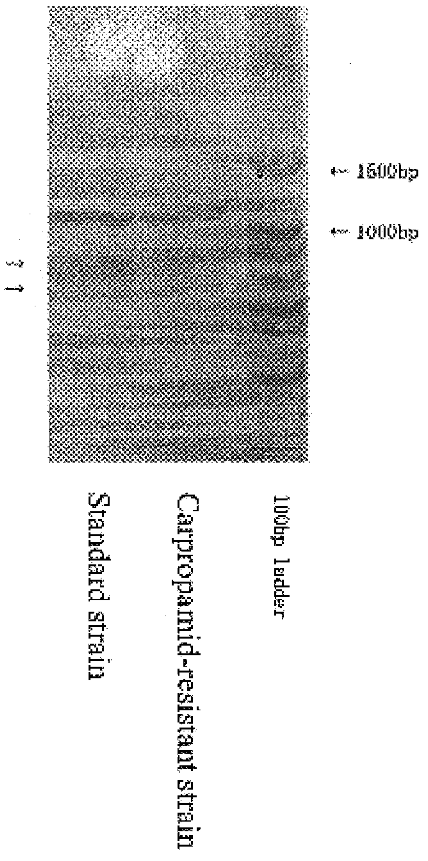

Then, the mixture of the reaction solution and the loading buffer were used to perform electrophoresis with the PhastSystem full automatic electrophoresis system from Amersham Biosciences. PhastGel Homogeneous 12.5 and PhastGel Native Buffer Strips from Amersham Biosciences were used as a gel carrier and a buffer reagent, respectively, for pre-electrophoresis at 400 V, 10 mA, 2.5 W, 4° C., and 100 Vh and for actual electrophoresis at 400 V, 10 mA, 2.5 W, 4° C., and 200 Vh. The results are shown in FIGS. 6A and 6B. FIG. 6A shows the results from electrophoresis without the above-described purification using GFX PCR DNA and the Gel Band Purification Kit. FIG. 6B shows the results from electrophoresis following the above-described purification using GFX PCR DNA and the Gel Band Purification Kit.

The electrophoresis patterns of the single stranded DNA are different in FIGS. 6A and 6B, presumably due to buffer compositions in the PCR solutions. In any case, difference in the electrophoresis patterns between the standard strain and the carpropamid-resistant strains was observed and distinguishable from FIGS. 6A and 6B.

Example 5

An expression vector incorporating the mutant SCDH gene was constructed to study its resistance to an SCDH inhibitor.

In order to incorporate a scytalone dehydratase gene from a rice blast fungus into a protein expression vector pGEX-2T (Amersham Biosciences), RT-PCR was conducted using Primer 7(5'-ATCGTCGACGTGAATTCGTCTTGTAAAAGCCGCCAAC-3') (SEQ ID NO: 11) and Primer 3 (5'-AGTTCGAACTGGAATTCAACCGGCACG- CATGATGCATGCATTTA-3') (SEQ ID NO: 7) having EcoRI cleavage sites at their terminals. The RT-PCR was conducted according to the method described in Example 1. Primers 7 and 3 were located upstream and downstream from the open reading frame (ORF) of the SCDH gene, respectively, so as to flank the whole coding region for the SCDH enzyme.

For RT-PCR, first, total RNA (2 μg each) extracted from the standard (wild-type) fungus or the carpropamid-resistant rice blast fungus were mixed with 2 μl oligo$(dT)_{20}$ (10 pmol/μl), 2 μl each of Primer 4 (25 pmol/μl) and Primer 3 (25 pmol/μl) and RT-PCR bead (Amersham Biosciences) to prepare a reaction solution for a final volume of 50 μl. The reaction took place under the following conditions. For cDNA strand synthesis, the reaction solutions were reacted at 42° C. for 30 minutes, followed by reaction at 95° C. for 30 minutes. Subsequently, PCR reaction was performed by repeating 25 cycles of 95° C. for 30 seconds, 55° C. for 1 minute and 72° C. for 1 minute. After the reaction, RT-PCR products were purified from the reaction solutions using GFX PCR DNA and the Gel Band Purification Kit (Amersham Biosciences) and then eluted with a final volume of 50 μl of sterilized water.

Next, 30 μl of the solution containing one of the RT-PCR products was mixed with 4 μl of 10×H buffer (Takara), 1 μl of EcoRI (12 u/μl, Takara) for a final volume of 40 μl and subjected to restriction enzyme reaction at 37° C. for 2 hours. After the restriction enzyme reaction, the reaction solutions were purified with GFX PCR DNA and the Gel Band Purification Kit (Amersham Biosciences) and eluted with 30 μl sterilized water.

In addition, 1 μg of GST-fused protein expression vector pGEX-2T (Amersham Biosciences) was mixed with 1 μl of 10×H buffer (Takara) and 1 μl of EcoRI (12 u/μl, Takara) for a final volume of 10 μl and subjected to a restriction enzyme reaction at 37° C. for 1 hour. To this reaction Solution, 10 μl of BAP buffer (TOYOBO), 2.5 μl of alkaline phosphatase (0.4 u/μl, BAP-101, TOYOBO) and 77.5 μl of sterilized water were added. The resultant was subjected to dephosphorylation reaction at 37° C. for 2 hours.

Figure 7:
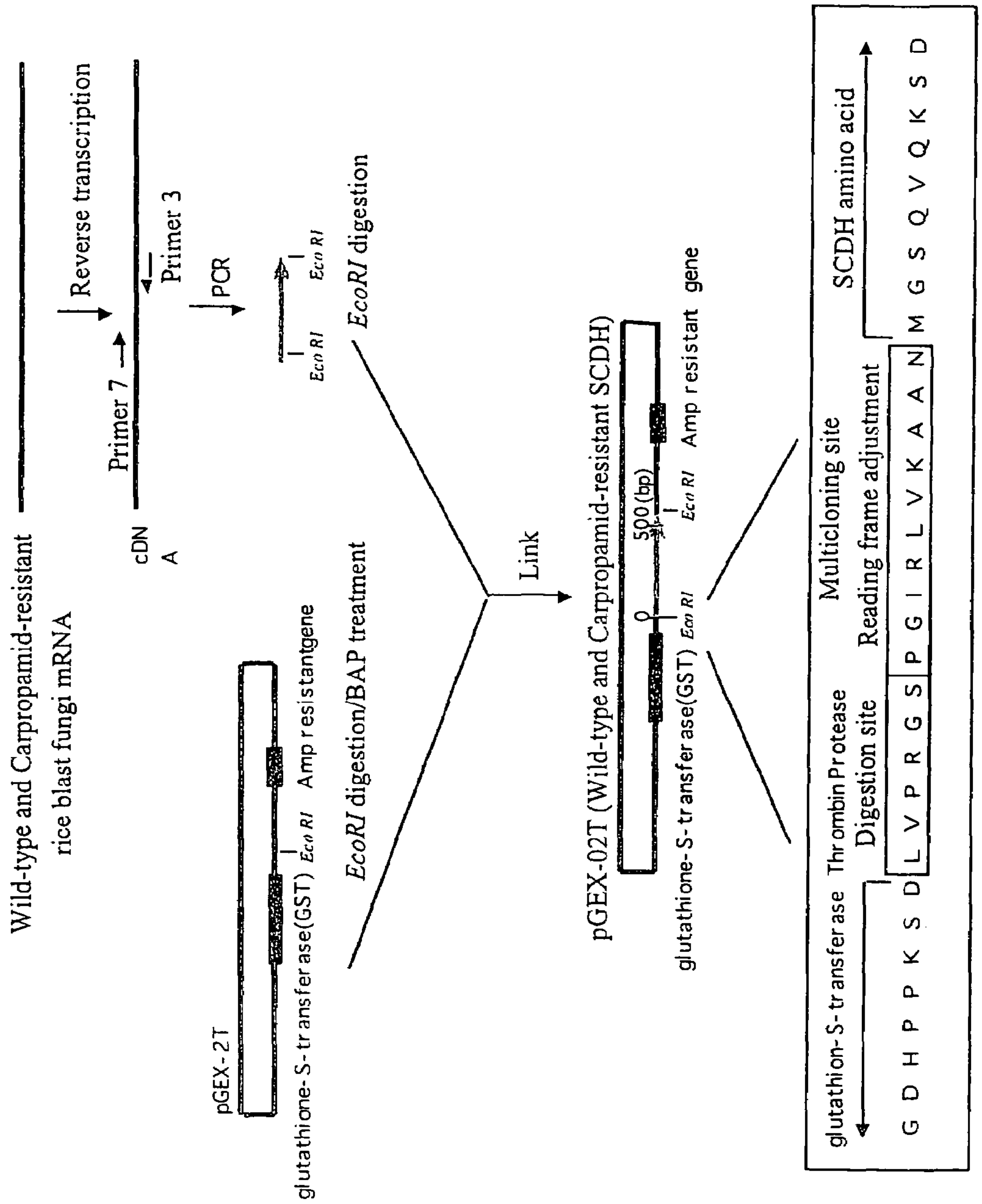
FIG. 7 is a schematic view showing a method for preparing plasmid Rice Blast wild SCDH cDNA and Rice Blast Mutant SCDH cDNA. Peptide sequence is SEQ ID NO: 19.

Then, reaction solutions were prepared by mixing 2 μl of the EcoRI-digested RT-PCR product, 1 μl of EcoRI/BAP-treated pGEX-2T, 2 μl sterilized water and 5 μl ligation buffer 1 (Ver. 2, Takara) and subjected to ligation reaction at 16° C. for 12 hours. After the reaction, by following the protocol attached to the competent cell of *E.coli* (strain JM109) (Takara), the reaction solutions were used to transform *E.coli* JM109. Then, the transformed *E.coli* JM109 were spread over LB solid media each containing 50 ppm ampicillin and subjected to static culture at 37° C. for 12 hours. After the cultivation, a few single colonies were scraped to perform direct colony PCR. As a result of the direct colony PCR, pGEX-2T inserted with the SCDH gene in the direction of interest were screened. The nucleotide sequence was further sequenced to confirm that the nucleotide sequence of the inserted SCDH gene was correct. This method is schematically illustrated in FIG. 7. The plasmid obtained according to this method was deposited with the International Patent Organism Depositary, National Institute of Advanced Industrial Science and Technology (Tsukuba Central 6, 1-1-1 Higashi, Tsukuba, Ibaraki, Japan) on Mar. 8, 2002 under the Budapest Treaty, as Rice Blast Mutant SCDH cDNA (FERM BP-7948).

Then, *E. coli* transformed with a pGEX-2T vector containing the correctly inserted SCDH gene was cultured at 27° C. in 200 ml LB liquid medium containing 50 ppm ampicillin until $OD_{260}$ became 0.6-1.0. Thereafter, isopropyl-1-thio-β-D-galactoside (IPTG) was added to a final concentration of 1 mM and further subjected to thorough agitation culture at 27° C. for 5 hours. After the cultivation, *E.coli* was collected by centrifugation (10,000×g, 10 minutes, 4° C.). *E.coli* was once suspended in 10 ml of cold 1/15 M potassium phosphate buffer (pH 6.8) for washing, and then collected by another centrifugation (10,000×g, 10 minutes, 4° C.). Subsequently, *E.coli* was again suspended in 5 ml of cold 1/15 M potassium phosphate buffer (pH 6.8), subjected to ultrasonic treatment using a microchip while icing, and centrifuged at 4° C., 15,000×g for 20 minutes. The supernatants were used as crude enzyme solutions.

Figure 8:
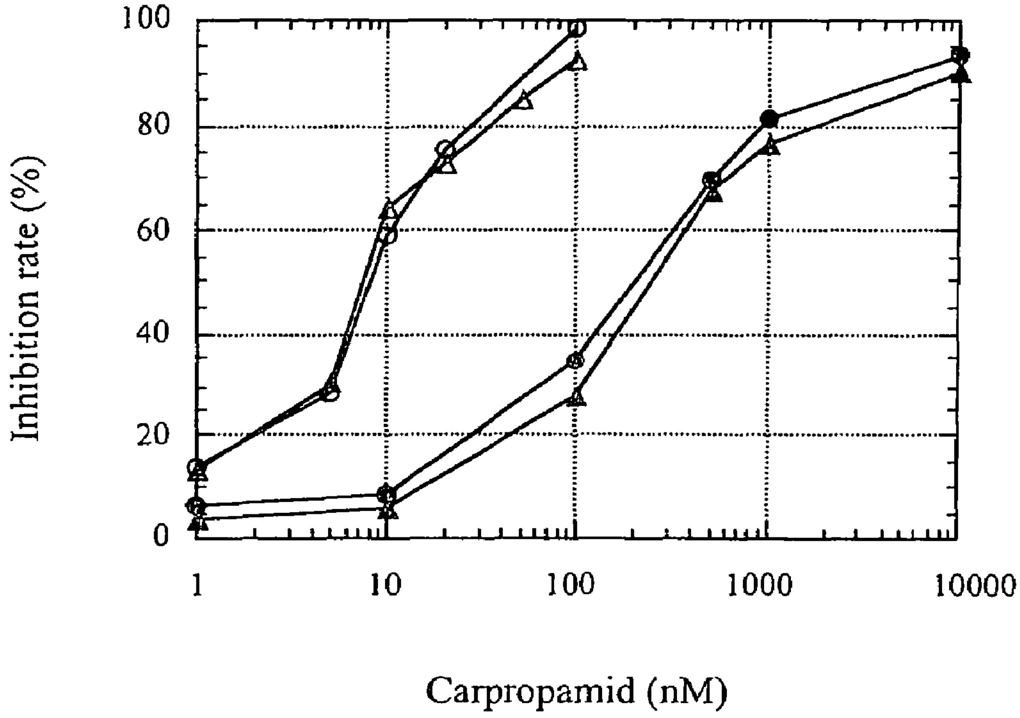
FIG. 8 is a characteristic diagram showing the relationship between the carpropamid concentrations and the inhibition rates for SCDH enzyme activity for the GST-fused SCDH enzyme obtained by expressing cDNA from the standard strain in *E.coli*, the GST-fused SCDH enzyme obtained by expressing cDNA from the resistant strain in *E.coli*, the crude enzyme solution from the standard strain and the crude enzyme solution from the resistant strain. In this diagram, the open circles represent the results for the crude enzyme solution from the standard strain, the open triangles represent the results for the GST-fused SCDH enzyme expressed from the standard strain cDNA, the closed circles represent the results for the crude enzyme solution from the resistant strain and the closed triangles represent the results for the GST-fused SCDH enzyme expressed from the resistant strain cDNA.

The crude enzyme solutions were used to determine sensitivity to carpropamid. The sensitivity to carpropamid was determined in the same manner as described in Example 1. The results are shown in FIG. 8. In FIG. 8, the open circles and closed circles represent the results from determination of sensitivity to carpropamid measured in Example 1.

Referring to FIG. 8, for both the standard fungus and carpropamid-resistant fungi, the GST-fused SCDH enzymes expressed in *E.coli* exhibited the same drug sensitivity as the SCDH enzyme contained in the crude enzyme solutions extracted from rice blast fungi.

Similarly, sensitivity to SCDH inhibitors, fenoxanil and diclocymet, were also studied. The results are shown in FIG. 9.

Figure 9:
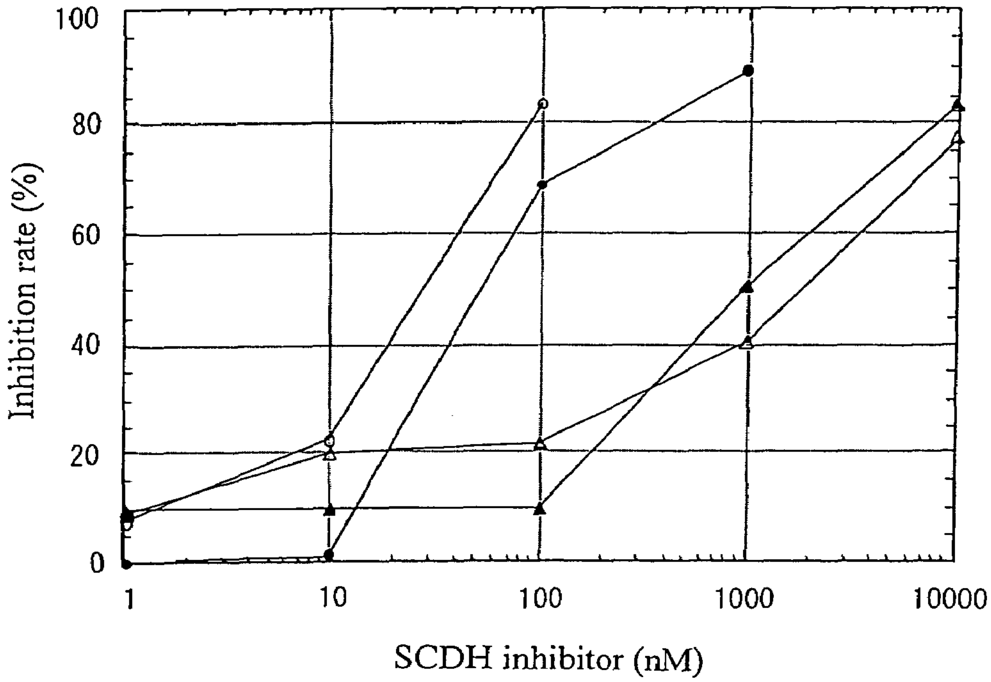
FIG. 9 is a characteristic diagram showing the relationship between the fenoxanil or diclocymet concentrations and the inhibition rates for the GST-fused SCDH enzyme obtained by expressing cDNA from the standard strain in *E.coli* and the GST-fused SCDH enzyme obtained by expressing cDNA from the resistant strain in *E.coli*. In this diagram, the open circles represent the inhibition of the GST-fused SCDH enzyme expressed from the standard strain cDNA by fenoxanil, the open triangles represent the inhibition of the GST-fused SCDH enzyme expressed from the resistant strain cDNA by fenoxanil, the closed circles represent the inhibition of the GST-fused SCDH enzyme expressed from the standard strain cDNA by diclocymet, and the closed triangles represent the inhibition of the GST-fused SCDH enzyme expressed from the resistant strain cDNA by diclocymet.

Referring to FIG. 9, the GST-fused SCDH enzyme was also found to show resistance to fenoxanil and diclocymet. In other words, the results shown in FIGS. 8 and 9 revealed that the GST-fused SCDH enzyme showed high enzyme activity in the presence of various SCDH inhibitors. Accordingly, in order to find and/or develop drugs for preventing and disinfestating for rice blast fungi that exhibit high infectivity to rice even in the presence of SCDH inhibitors, candidate agents may be screened using the GST-fused SCDH enzyme. Specifically, the enzyme activity of the GST-fused SCDH enzyme is measured in the presence of candidate agents to select a candidate agent that significantly decreases the enzyme activity. The selected candidate agent decreases the enzyme activity of the mutant SCDH enzyme and thus decreases the infectivity of the resistant rice blast fungus. Accordingly, development of rice blast caused by resistant rice blast fungi can be prevented.

Example 6

A simple assay for Val75Met mutation in an SCDH enzyme from a rice blast fungus was considered by applying the PCR-RFLP method. Similar to Example 3, a rice blast fungus filamentous mycelium was irradiated with microwaves to simply prepare a genome DNA solution. Five μl of this genome DNA solution was mixed with 1 μl each of Primer 8 (SEQ ID NO: 12, 5'-TTCGTCGGCATGGTCTCGAGCATCTAG-3', 25pmol/μl), Primer 5 (5'-GTGGCCCTTCATGGTGACCTCCT-3', ≅pmol/μl) (SEQ ID NO: 9) and PCR bead (Amersham Bioscience) for a final volume of 25 μl to prepare a reaction solution.

The underlined bases “TCT” in Primer 8 mismatch the nucleotide sequence of the genome DNA as a template and are designed to form a cleavage recognized site (“TCTAGA”) for restriction enzyme XbaI together with the bases “AG” at the 3'-end and the first base that is amplified by the later-described PCR. When the first base amplified by the PCR is “A,” the fragment amplified by Primer 8 will include the cleavage recognized site for restriction enzyme XbaI. On the other hand, when the first base amplified by the PCR is a base other than “A,” the cleavage recognized site for restriction enzyme XbaI is absent in the amplified fragment.

Figure 10:
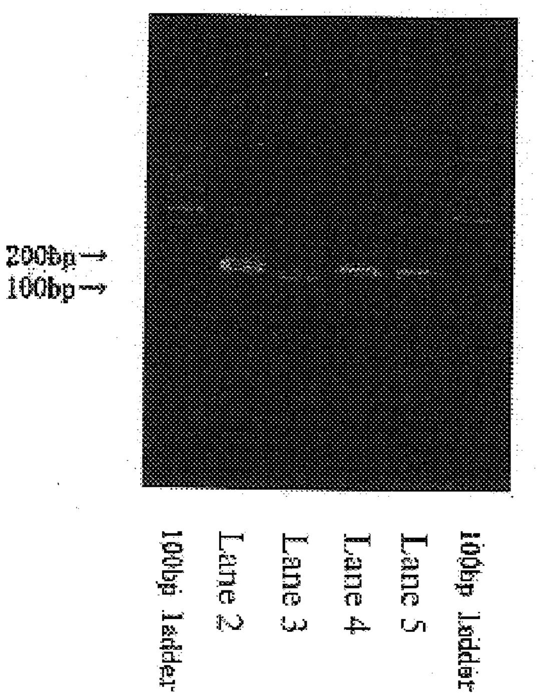
FIG. 10 is an electrophoresis (3% agarose gel) picture showing the results obtained by analyzing Val75Met mutation in the SCDH enzyme by applying PCR-RFLP method performed in Example 6.

For PCR reaction, 40 cycles of 95° C. for 30 seconds, 55° C. for 1 minute and 72° C. for 2 minute were repeated. After the final cycle at 72° C. for 7 minutes, the reaction was carried out and terminated. As a result of this reaction, a PCR product of 183 bp was obtained. The PCR product was purified using GFX PCR DNA and the Gel Band Purification Kit (Amersham Biosciences) and then eluted with a final volume of 20 μl of sterilized water. Of the resultant, 7.5 μl was mixed with 1 μl 10×M buffer (Takara), 1 μl 0.1% BSA solution and 0.5 μl XbaI (12 u/μl, Takara) for a final volume of 10 μl and subjected to restriction enzyme reaction at 37° C. for 1 hour. Results from electrophoresis of the total volume of the reaction solution in 3% agarose are shown in FIG. 10. In FIG. 10, Lane 2 represents the reaction solution using the genome DNA extracted from the standard strain. Lane 3 represents the reaction solution using the genome DNA extracted from the resistant strain. Lane 4 represents the reaction solution using the genome DNA extracted from the standard strain, which had not been subjected to restriction enzyme reaction. Lane 5 represents the reaction solution using the genome DNA extracted from the resistant strain, which had not been subjected to restriction enzyme reaction.

As can be appreciated from FIG. 10, the XbaI-treated sample of the PCR product from the resistant strain was shorter by about 25 bases. From this result, it became clear that the standard strain (wild-type strain) and the resistant strain can be distinguished by applying the PCR-RFLP technique.

INDUSTRIAL APPLICABILITY

As described above, the present invention provides a gene that can be used extensively, for example, in studies relating to rice blast fungi resistant to SCDH inhibitors. This gene may be used, for example, in screening a novel SCDH inhibitor and assessing sensitivity of a subject rice blast fungus to an SCDH inhibitor.

Free Text in Sequence Listing

SEQ ID NOS: 5-12 are synthesized primers.

What is claimed is:

1. An isolated or purified gene coding for either one of the following proteins (a) or (b):

(a) a protein consisting of the amino acid sequence of SEQ ID NO: 2; or (b) a protein consisting of an amino acid sequence wherein said amino acid sequence is a variant of SEQ ID NO: 2 which differs from SEQ ID NO: 2 solely by deletion, substitution or addition of 1 to 10 amino acids in SEQ ID NO: 2, wherein the amino acid at the position corresponding to position 75 of SEQ ID NO: 2 is methionine, and wherein said protein has scytalone dehydratase activity in the presence of a scytalone dehydratase inhibitor.

2. The gene according to claim 1, wherein the scytalone dehydratase inhibitor inhibits the dehydration reaction from scytalone to 1,3,8-trihydroxynaphtalene in a melanin biosynthesis pathway.

3. The gene according to claim 1, wherein the scytalone dehydratase inhibitor is carpropamid.

4. A recombinant vector comprising a gene coding for either one of the following proteins (a) or (b):

(a) a protein consisting of the amino acid sequence of SEQ ID NO: 2; or (b) a protein consisting of an amino acid sequence wherein said amino acid sequence is a variant of SEQ ID NO: 2 which differs from SEQ ID NO: 2 solely by deletion, substitution or addition of 1 to 10 amino acids in SEQ ID NO: 2, wherein the amino acid at the position corresponding to position 75 of SEQ ID NO: 2 is methionine, and wherein said protein has scytalone dehydratase activity in the presence of a scytalone dehydratase inhibitor.

5. An isolated transformed cell obtained by transformation with the recombinant vector of claim 4.

6. An isolated or purified gene coding for a protein comprising the amino acid sequence of SEQ ID NO:2.

7. The isolated or purified gene of claim 6, wherein the protein consists of SEQ ID NO:2.

8. A recombinant vector comprising a gene coding for a protein comprising the amino acid sequence of SEQ ID NO: 2.

9. An isolated transformed cell obtained by transformation with the recombinant vector of claim 8.

10. An isolated or purified gene coding for a protein consisting of an amino acid sequence wherein said amino acid sequence is a variant of SEQ ID NO: 2 which differs from SEQ ID NO: 2 solely by deletion, substitution or addition of 1 to 10 amino acids in SEQ ID NO: 2, wherein the amino acid at the position corresponding to position 75 of SEQ ID NO: 2 is methionine, and wherein said protein has scytalone dehydratase activity in the presence of a scytalone dehydratase inhibitor.

* * * * *

```
                         SEQUENCE LISTING


<160> NUMBER OF SEQ ID NOS: 19

<210> SEQ ID NO 1
<211> LENGTH: 516
<212> TYPE: DNA
<213> ORGANISM: Pyricularia oryzae
<220> FEATURE:
<221> NAME/KEY: CDS
<222> LOCATION: (1)..(516)

<400> SEQUENCE: 1

atg ggt tcg caa gtt caa aag agc gat gag ata acc ttc tca gac tac       48
Met Gly Ser Gln Val Gln Lys Ser Asp Glu Ile Thr Phe Ser Asp Tyr
  1               5                  10                  15

ctg ggc ctc atg act tgc gtc tat gag tgg gca gac agc tac gac tcc       96
Leu Gly Leu Met Thr Cys Val Tyr Glu Trp Ala Asp Ser Tyr Asp Ser
             20                  25                  30

aag gac tgg gat agg ctg cga aag gtc att gcg cct act ctg cgc att      144
Lys Asp Trp Asp Arg Leu Arg Lys Val Ile Ala Pro Thr Leu Arg Ile
         35                  40                  45

gac tac cgc tcc ttc ctc gac aag ctc tgg gag gca atg ccg gcc gag      192
Asp Tyr Arg Ser Phe Leu Asp Lys Leu Trp Glu Ala Met Pro Ala Glu
     50                  55                  60

gag ttc gtc ggc atg gtc tcg agc aag cag atg ctg ggc gac ccc acc      240
Glu Phe Val Gly Met Val Ser Ser Lys Gln Met Leu Gly Asp Pro Thr
 65                  70                  75                  80

ctc cgc acg cag cac ttc atc ggc ggc acg cgc tgg gag aag gtg tcc      288
Leu Arg Thr Gln His Phe Ile Gly Gly Thr Arg Trp Glu Lys Val Ser
                 85                  90                  95

gag gac gag gtc atc ggc tac cac cag ctg cgc gtc ccg cac cag agg      336
Glu Asp Glu Val Ile Gly Tyr His Gln Leu Arg Val Pro His Gln Arg
            100                 105                 110

tac aag gac acc acc atg aag gag gtc acc atg aag ggc cac gcc cac      384
Tyr Lys Asp Thr Thr Met Lys Glu Val Thr Met Lys Gly His Ala His
        115                 120                 125

tcg gca aac ctt cac tgg tac aag aag atc gac ggc gtc tgg aag ttc      432
Ser Ala Asn Leu His Trp Tyr Lys Lys Ile Asp Gly Val Trp Lys Phe
    130                 135                 140
```

-continued

```
gcc ggc ctc aag ccc gat atc cgc tgg ggc gag ttc gac ttt gac agg      480
Ala Gly Leu Lys Pro Asp Ile Arg Trp Gly Glu Phe Asp Phe Asp Arg
145                 150                 155                 160

atc ttt gag gac gga cgg gag acc ttt ggc gac aaa                      516
Ile Phe Glu Asp Gly Arg Glu Thr Phe Gly Asp Lys
                165                 170


<210> SEQ ID NO 2
<211> LENGTH: 172
<212> TYPE: PRT
<213> ORGANISM: Pyricularia oryzae

<400> SEQUENCE: 2

Met Gly Ser Gln Val Gln Lys Ser Asp Glu Ile Thr Phe Ser Asp Tyr
  1               5                  10                  15

Leu Gly Leu Met Thr Cys Val Tyr Glu Trp Ala Asp Ser Tyr Asp Ser
             20                  25                  30

Lys Asp Trp Asp Arg Leu Arg Lys Val Ile Ala Pro Thr Leu Arg Ile
         35                  40                  45

Asp Tyr Arg Ser Phe Leu Asp Lys Leu Trp Glu Ala Met Pro Ala Glu
     50                  55                  60

Glu Phe Val Gly Met Val Ser Ser Lys Gln Met Leu Gly Asp Pro Thr
 65                  70                  75                  80

Leu Arg Thr Gln His Phe Ile Gly Gly Thr Arg Trp Glu Lys Val Ser
                 85                  90                  95

Glu Asp Glu Val Ile Gly Tyr His Gln Leu Arg Val Pro His Gln Arg
            100                 105                 110

Tyr Lys Asp Thr Thr Met Lys Glu Val Thr Met Lys Gly His Ala His
        115                 120                 125

Ser Ala Asn Leu His Trp Tyr Lys Lys Ile Asp Gly Val Trp Lys Phe
    130                 135                 140

Ala Gly Leu Lys Pro Asp Ile Arg Trp Gly Glu Phe Asp Phe Asp Arg
145                 150                 155                 160

Ile Phe Glu Asp Gly Arg Glu Thr Phe Gly Asp Lys
                165                 170


<210> SEQ ID NO 3
<211> LENGTH: 516
<212> TYPE: DNA
<213> ORGANISM: Pyricularia oryzae
<220> FEATURE:
<221> NAME/KEY: CDS
<222> LOCATION: (1)..(516)

<400> SEQUENCE: 3

atg ggt tcg caa gtt caa aag agc gat gag ata acc ttc tca gac tac       48
Met Gly Ser Gln Val Gln Lys Ser Asp Glu Ile Thr Phe Ser Asp Tyr
  1               5                  10                  15

ctg ggc ctc atg act tgc gtc tat gag tgg gca gac agc tac gac tcc       96
Leu Gly Leu Met Thr Cys Val Tyr Glu Trp Ala Asp Ser Tyr Asp Ser
             20                  25                  30

aag gac tgg gat agg ctg cga aag gtc att gcg cct act ctg cgc att      144
Lys Asp Trp Asp Arg Leu Arg Lys Val Ile Ala Pro Thr Leu Arg Ile
         35                  40                  45

gac tac cgc tcc ttc ctc gac aag ctc tgg gag gca atg ccg gcc gag      192
Asp Tyr Arg Ser Phe Leu Asp Lys Leu Trp Glu Ala Met Pro Ala Glu
     50                  55                  60

gag ttc gtc ggc atg gtc tcg agc aag cag gtg ctg ggc gac ccc acc      240
Glu Phe Val Gly Met Val Ser Ser Lys Gln Val Leu Gly Asp Pro Thr
 65                  70                  75                  80
```

-continued

```
ctc cgc acg cag cac ttc atc ggc ggc acg cgc tgg gag aag gtg tcc      288
Leu Arg Thr Gln His Phe Ile Gly Gly Thr Arg Trp Glu Lys Val Ser
                85                  90                  95

gag gac gag gtc atc ggc tac cac cag ctg cgc gtc ccg cac cag agg      336
Glu Asp Glu Val Ile Gly Tyr His Gln Leu Arg Val Pro His Gln Arg
            100                 105                 110

tac aag gac acc acc atg aag gag gtc acc atg aag ggc cac gcc cac      384
Tyr Lys Asp Thr Thr Met Lys Glu Val Thr Met Lys Gly His Ala His
        115                 120                 125

tcg gca aac ctt cac tgg tac aag aag atc gac ggc gtc tgg aag ttc      432
Ser Ala Asn Leu His Trp Tyr Lys Lys Ile Asp Gly Val Trp Lys Phe
    130                 135                 140

gcc ggc ctc aag ccc gat atc cgc tgg ggc gag ttc gac ttt gac agg      480
Ala Gly Leu Lys Pro Asp Ile Arg Trp Gly Glu Phe Asp Phe Asp Arg
145                 150                 155                 160

atc ttt gag gac gga cgg gag acc ttt ggc gac aaa                      516
Ile Phe Glu Asp Gly Arg Glu Thr Phe Gly Asp Lys
                165                 170


<210> SEQ ID NO 4
<211> LENGTH: 172
<212> TYPE: PRT
<213> ORGANISM: Pyricularia oryzae

<400> SEQUENCE: 4

Met Gly Ser Gln Val Gln Lys Ser Asp Glu Ile Thr Phe Ser Asp Tyr
  1               5                  10                  15

Leu Gly Leu Met Thr Cys Val Tyr Glu Trp Ala Asp Ser Tyr Asp Ser
            20                  25                  30

Lys Asp Trp Asp Arg Leu Arg Lys Val Ile Ala Pro Thr Leu Arg Ile
        35                  40                  45

Asp Tyr Arg Ser Phe Leu Asp Lys Leu Trp Glu Ala Met Pro Ala Glu
     50                  55                  60

Glu Phe Val Gly Met Val Ser Ser Lys Gln Val Leu Gly Asp Pro Thr
 65                  70                  75                  80

Leu Arg Thr Gln His Phe Ile Gly Gly Thr Arg Trp Glu Lys Val Ser
                85                  90                  95

Glu Asp Glu Val Ile Gly Tyr His Gln Leu Arg Val Pro His Gln Arg
            100                 105                 110

Tyr Lys Asp Thr Thr Met Lys Glu Val Thr Met Lys Gly His Ala His
        115                 120                 125

Ser Ala Asn Leu His Trp Tyr Lys Lys Ile Asp Gly Val Trp Lys Phe
    130                 135                 140

Ala Gly Leu Lys Pro Asp Ile Arg Trp Gly Glu Phe Asp Phe Asp Arg
145                 150                 155                 160

Ile Phe Glu Asp Gly Arg Glu Thr Phe Gly Asp Lys
                165                 170


<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: chemically
      synthesized primer

<400> SEQUENCE: 5

gcagtgatac ccacaccaaa g                                               21
```

-continued

<210> SEQ ID NO 6
<211> LENGTH: 22
<212> TYPE: DNA
<213> ORGANISM: Artificial Sequence
<220> FEATURE:
<223> OTHER INFORMATION: Description of Artificial Sequence: chemically synthesized primer

<400> SEQUENCE: 6
ttatttgtcg gcaaaggtct cc 22

<210> SEQ ID NO 7
<211> LENGTH: 44
<212> TYPE: DNA
<213> ORGANISM: Artificial Sequence
<220> FEATURE:
<223> OTHER INFORMATION: Description of Artificial Sequence: chemically synthesized primer

<400> SEQUENCE: 7
agttcgaact ggaattcaac cggcacgcat gatgcatgca ttta 44

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: chemically synthesized primer

<400> SEQUENCE: 8
atgggttcgc aagttcaaaa g 21

<210> SEQ ID NO 9
<211> LENGTH: 23
<212> TYPE: DNA
<213> ORGANISM: Artificial Sequence
<220> FEATURE:
<223> OTHER INFORMATION: Description of Artificial Sequence: chemically synthesized primer

<400> SEQUENCE: 9
gtggcccttc atggtgacct cct 23

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: chemically synthesized primer

<400> SEQUENCE: 10
acaagctctg ggaggcaatg 20

<210> SEQ ID NO 11
<211> LENGTH: 37
<212> TYPE: DNA
<213> ORGANISM: Artificial Sequence
<220> FEATURE:
<223> OTHER INFORMATION: Description of Artificial Sequence: chemically synthesized primer

<400> SEQUENCE: 11
atcgtcgacg tgaattcgtc ttgtaaaagc cgccaac 37

-continued

<210> SEQ ID NO 12
<211> LENGTH: 27
<212> TYPE: DNA
<213> ORGANISM: Artificial Sequence
<220> FEATURE:
<223> OTHER INFORMATION: Description of Artificial Sequence: chemically synthesized primer

<400> SEQUENCE: 12
ttcgtcggca tggtctcgag catctag 27

<210> SEQ ID NO 13
<211> LENGTH: 600
<212> TYPE: DNA
<213> ORGANISM: Pyricularia oryzae

<400> SEQUENCE: 13
ctagcaaccg cagtgatacc cacaccaaag agcttccttc agtctagtat agttcacttc 60
aacttgtaaa agccgccaac atgggttcgc aagttcaaaa gagcgatgag ataaccttct 120
cagactacct gggcctcatg acttgcgtct atgagtgggc agacagctac gactccaagg 180
actgggatag gctgcgaaag gtcattgcgc ctactctgcg cattgactac cgctccttcc 240
tcgacaagct ctgggaggca atgccggccg aggagttcgt cggcatggtc tcgagcaagc 300
aggtgctggg cgaccccacc ctccgcacgc agcacttcat cggcggcacg cgctgggaga 360
aggtgtccga ggacgaggtc atcggctacc accagctgcg cgtcccgcac cagaggtaca 420
aggacaccac catgaaggag gtcaccatga agggccacgc ccactcggca aaccttcact 480
ggtacaagaa gatcgacggc gtctggaagt tcgccggcct caagcccgat atccgctggg 540
gcgagttcga ctttgacagg atctttgagg acggacggga gacctttggc gacaaataaa 600

<210> SEQ ID NO 14
<211> LENGTH: 545
<212> TYPE: DNA
<213> ORGANISM: Pyricularia oryzae

<400> SEQUENCE: 14
ctagtatagt tcacttcaac ttgtaaaagc cgccaacatg ggttcgcaag ttcaaaagag 60
cgatgagata accttctcag actacctggg cctcatgact tgcgtctatg agtgggcaga 120
cagctacgac tccaaggact gggataggct gcgaaaggtc attgcgccta ctctgcgcat 180
tgactaccgc tccttcctcg acaagctctg ggaggcaatg ccggccgagg agttcgtcgg 240
catggtctcg agcaagcagg tgctgggcga ccccaccctc cgcacgcagc acttcatcgg 300
cggcacgcgc tgggagaagg tgtccgagga cgaggtcatc ggctaccacc agctgcgcgt 360
cccgcaccag aggtacaagg acaccaccat gaaggaggtc accatgaagg gccacgccca 420
ctcggcaaac cttcactggt acaagaagat cgacggcgtc tggaagttcg ccggcctcaa 480
gcccgacatc cgctggggcg agttcgactt tgacaggatc tttgaggacg gacgggagac 540
ctttg 545

<210> SEQ ID NO 15
<211> LENGTH: 538
<212> TYPE: DNA
<213> ORGANISM: Pyricularia oryzae

<400> SEQUENCE: 15
agttcacttc aacttgtaaa agccgccaac atgggttcgc aagttcaaaa gagcgatgag 60
ataaccttct cagactacct gggcctcatg acttgcgtct atgagtgggc agacagctac 120

-continued

```
gactccaagg actgggatag gctgcgaaag gtcattgcgc ctactctgcg cattgactac    180

cgctccttcc tcgacaagct ctgggaggca atgccggccg aggagttcgt cggcatggtc    240

tcgagcaagc aggtgctggg cgaccccacc ctccgcacgc agcacttcat cggcggcacg    300

cgctgggaga aggtgtccga ggacgaggtc atcggctacc accagctgcg cgtcccgcac    360

cagaggtaca aggacaccac catgaaggag gtcaccatga agggccacgc ccactcggca    420

aaccttcact ggtacaagaa gatcgacggc gtctggaagt tcgccggcct caagcccgac    480

atccgctggg gcgagttcga ctttgacagg atctttgagg acggacggga gacctttg      538
```

```
<210> SEQ ID NO 16
<211> LENGTH: 610
<212> TYPE: DNA
<213> ORGANISM: Pyricularia oryzae

<400> SEQUENCE: 16

ctagcaaccg cagtgatacc cacaccaaag agcttccttc agtctagtat agttcacttc     60

aacttgtaaa agccgccaac atgggttcgc aagttcaaaa gagcgatgag ataaccttct    120

cagactacct gggcctcatg acttgcgtct atgagtgggc agacagctac gactccaagg    180

actgggatag gctgcgaaag gtcattgcgc ctactctgcg cattgactac cgctccttcc    240

tcgacaagct ctgggaggca atgccggccg aggagttcgt cggcatggtc tcgagcaagc    300

aggtgctggg cgaccccacc ctccgcacgc agcacttcat cggcggcacg cgctgggaga    360

aggtgtccga ggacgaggtc atcggctacc accagctgcg cgtcccgcac cagaggtaca    420

aggacaccac catgaaggag gtcaccatga agggccacgc ccactcggca aaccttcact    480

ggtacaagaa gatcgacggc gtctggaagt tcgccggcct caagcccgat atccgctggg    540

gcgagttcga ctttgacagg atctttgagg acggacggga gacctttggc gacaaataaa    600

tgcatgcatc                                                           610
```

```
<210> SEQ ID NO 17
<211> LENGTH: 732
<212> TYPE: DNA
<213> ORGANISM: Pyricularia oryzae

<400> SEQUENCE: 17

tccttcagtc tagtatagtt cacttcaact tgtaaaagcc gccaacatgg gttcgcaagt     60

tcaaaagagc gatgagataa ccttctcagg tgagcataat atccccctcc aaaaagaaaa    120

tagcggtgaa gccaccaacg acagtaccgc tgaccctaat tcccctccag actacctggg    180

cctcatgact tgcgtctatg agtgggcaga cagctacgac tccaaggact gggataggct    240

gcgaaaggtc attgcgccta ctctgcgcgt atgttccgcc ctgccatgtt tatttttact    300

ttcccacacc aaatccagac tttaacagcg acgaccaaaa aaaaaaaaaa aaaacagatt    360

gactaccgct ccttcctcga caagctctgg gaggcaatgc cggccgagga gttcgtcggc    420

atggtctcga gcaagcaggt gctgggcgac cccaccctcc gcacgcagca cttcatcggc    480

ggcacgcgct gggagaaggt gtccgaggac gaggtcatcg gctaccacca gctgcgcgtc    540

ccgcaccaga ggtacaagga caccaccatg aaggaggtca ccatgaaggg ccacgcccac    600

tcggcaaacc ttcactggta caagaagatc gacggcgtct ggaagttcgc cggcctcaag    660

cccgacatcc gctggggcga gttcgacttt gacaggatct ttgaggacgg acgggagacc    720

tttggcgaca aa                                                        732
```

-continued

```
<210> SEQ ID NO 18
<211> LENGTH: 729
<212> TYPE: DNA
<213> ORGANISM: Pyricularia oryzae

<400> SEQUENCE: 18

ttccttcagt ctagtatagt tcacttcaac ttgtaaaagc cgccaacatg ggttcgcaag      60

ttcaaaagag cgatgagata accttctcag gtgagcataa tatccccctc caaaaagaaa     120

atagcggtga agccaccaac gacagtaccg ctgaccctaa ttcccctcca gactacctgg     180

gcctcatgac ttgcgtctat gagtgggcag acagctacga ctccaaggac tgggataggc     240

tgcgaaaggt cattgcgcct actctgcgcg tatgttccgc cctgccatgt ttatttttac     300

tttcccacac caaatccaga ctttaacagc gacgaccaaa aaaaaaaaaa acagattgac     360

taccgctcct tcctcgacaa gctctgggag gcaatgccgg ccgaggagtt cgtcggcatg     420

gtctcgagca agcaggtgct gggcgacccc accctccgca cgcagcactt catcggcggc     480

acgcgctggg agaaggtgtc cgaggacgag gtcatcggct accaccagct gcgcgtcccg     540

caccagaggt acaaggacac caccatgaag gaggtcacca tgaagggcca cgcccactcg     600

gcaaaccttc actggtacaa gaagatcgac ggcgtctgga agttcgccgg cctcaagccc     660

gacatccgct ggggcgagtt cgactttgac aggatctttg aggacggacg ggagaccttt     720

ggcgacaaa                                                             729


<210> SEQ ID NO 19
<211> LENGTH: 33
<212> TYPE: PRT
<213> ORGANISM: Artificial Sequence
<220> FEATURE:
<223> OTHER INFORMATION: Description of Artificial Sequence: Synthetic
      peptide derived from Pyricularia oryzae

<400> SEQUENCE: 19

Gly Asp His Pro Pro Lys Ser Asp Leu Val Pro Arg Gly Ser Pro Gly
1               5                   10                  15

Ile Arg Leu Val Lys Ala Ala Asn Met Gly Ser Gln Val Gln Lys Ser
            20                  25                  30

Asp
```